United States Patent [19]

Watanabe et al.

[11] Patent Number: 4,647,520

[45] Date of Patent: Mar. 3, 1987

[54] ELECTROPHOTOGRAPHIC PHOTORECEPTOR CONTAINING AN AZO COMPOUND

[75] Inventors: Kazumasa Watanabe, Koganei; Satoru Ikeuchi, Hino; Osamu Sasaki; Naohiro Hirose, both Hachioji, all of Japan

[73] Assignee: Konoshiroku Photo Industry Co., Ltd., Japan

[21] Appl. No.: 780,721

[22] Filed: Sep. 27, 1985

Related U.S. Application Data

[63] Continuation of Ser. No. 672,209, Nov. 16, 1984, abandoned.

[30] Foreign Application Priority Data

Nov. 18, 1983 [JP] Japan ................................ 59-218227
Nov. 18, 1983 [JP] Japan ................................ 59-218228
Nov. 18, 1983 [JP] Japan ................................ 59-218229
Nov. 18, 1983 [JP] Japan ................................ 59-218230

[51] Int. Cl.⁴ .......................................... G03G 5/06
[52] U.S. Cl. ....................................... 430/58; 430/72; 430/75; 430/78
[58] Field of Search ................ 430/58, 72, 74, 75, 430/76, 78

[56] References Cited

U.S. PATENT DOCUMENTS 3,798,031  3/1974  Janssens et al. .................... 430/76
4,299,896  11/1981  Hashimoto et al. ................ 430/78

Primary Examiner—John L. Goodrow
Attorney, Agent, or Firm—Finnegan, Henderson, Farabow, Garrett & Dunner

[57] ABSTRACT

A photoreceptor comprising a photosensitive layer and an electroconductive support, wherein the photosensitive layer contains an azo compound represented by the following Formula [I]:

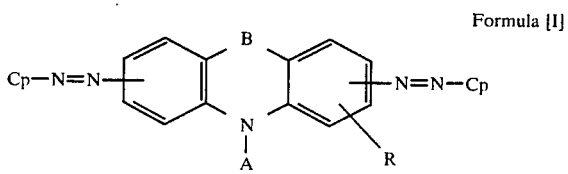

Formula [I]

wherein A is a substituted or unsubstituted alkyl group, or a substituted or unsubstituted aryl group, B is an oxygen atom or a sulfur atom; R is a hydrogen atom, an alkyl group, an alkoxy group, or a halogen atom; and Cp is

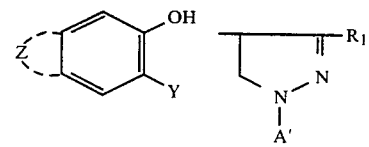

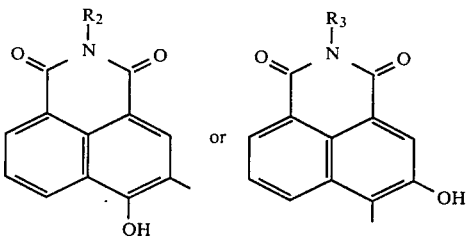

wherein
Z represents a group of atoms necessary for constituting a substituted or unsubstituted aromatic carbon ring, or a substituted or unsubstituted aromatic heterocyclic ring; Y is a substituted or unsubstituted carbamoyl group or a substituted or unsubstituted sulfamoyl group;
$R_1$ is a hydrogen atom, a substituted or unsubstituted amino group, a substituted or unsubstituted carbamoyl group, a carboxy group and the esters thereof, or cyano group; A' is a substituted or unsubstituted aryl group;
$R_2$ and $R_3$ are a substituted or unsubstituted alkyl group, or a substituted or unsubstituted aralkyl group, or a substituted or unsubstituted aryl group, respectively.

26 Claims, 6 Drawing Figures

ELECTROPHOTOGRAPHIC PHOTORECEPTOR CONTAINING AN AZO COMPOUND

This application is a continuation of application Ser. No. 672,209, filed Nov. 16, 1984, now abandoned.

BACKGROUND OF THE INVENTION

1. Field of the Invention

The present invention relates to a photoreceptor, and more particularly to a novel electrophotographic photoreceptor comprising a photosensitive layer containing an azo compound.

2. Description of the Prior Art

As the photoreceptor, inorganic photoreceptors having a photosensitive layer comprised principally of an inorganic photoconductive compound such as selenium, zinc oxide, cadmium sulfide, or the like, have heretofore been used widely. These photoreceptors, however, are not necessarily satisfactory with respect to their speed, thermal stability, moisture resistance, durability, and the like. For example, selenium, when crystallized, becomes deteriorated in the characteristics as the photoreceptor, and has therefore difficulty in the production thereof. The crystallization is sometimes caused by heat or finger prints, resulting in the deterioration of the characteristics of selenium as the photoreceptor. Cadmium sulfide is disadvantageous with respect to the moisture resistance and durability thereof. Zinc oxide also has drawbacks with respect to durability and the like.

In recent years, the research and development of new organic photoreceptors having a photosensitive layer composed principally of various organic photoconductive compounds have been made for the purpose of overcoming such shortcomings of these inorganic photoreceptors. For example, Japanese Patent Examined Publication No. 10496/1975 describes an organic photoreceptor having a photosensitive layer containing poly-N-vinylcarbazole and 2,4,7-trinitro-9-fluorenone. This photoreceptor, however, is not necessarily satisfactory in speed and durability. In order to improve such disadvantages, an attempt is made to develop a higher performance organic photoreceptor, whose carrier-generating function and carrier-transport function are allotted to different materials.

Such function-separated-type electrophotographic photoreceptors permit the selection of materials thereof from an extensive range, thus facilitating relatively the production of optional characteristic photoreceptors. For this reason, many studies have been made on photoreceptors of this type.

For the function-separated-type electrophotographic photoreceptor, a number of compounds are proposed as the carrier-generating material. An example of inorganic compounds that can be used as the carrier-generating material is amorphous selenium as described in Japanese Patent Examined Publication No. 16198/1968. This is to be used in combination with an organic photoconductive compound, but does not eliminate the disadvantage that the carrier-generating layer composed of amorphous selenium is crystallized when heated, whereby its characteristics as the photoreceptor is deteriorated.

Many electrophotographic photoreceptors which use organic dyes or pigments as the carrier-generating material also have been proposed. For example, those electrophotographic photoreceptors containing bisazo or trisazo compounds are disclosed in Japanese Patent Publication Open to Public Inspection (hereinafter referred to as Japanese Patent O.P.I. Publication) Nos. 12742/1979, 74746/1982 and 69148/1980. These bisazo or trisazo compounds, however, do not necessarily provide satisfactory characteristics such as speed, residual electric potential and stability when used repeatedly, and they restrict the carrier-transport material-selectable range, thus satisfying no adequately wide requirements for the electrophotographic process.

Further, in recent years, gas lasers such as the Ar laser, He-Ne laser, etc., and semiconductor lasers have now been used. These lasers are characterized by being ON/OFF turnable in time series, and are particularly promising as the light source for those printers such as intelligent copiers, image-processing function-having copiers, and computer output printers. Of these, the semiconductor laser requires no electric signal/optical signal conversion element such as the acoustooptic element, etc., and can be made compact and lightweight, thus having come to attention. The semiconductor laser, however, produces a lower output than does the gas laser, and has a longer oscillation wavelength (longer than about 780 nm). Accordingly, the semiconductor laser as it is can not be applied to those conventional photoreceptors whose spectral sensitivity is on the much shorter wavelength side than the oscillation wavelength.

SUMMARY OF THE INVENTION

It is therefore an object of the present invention to provide a photoreceptor which is stable to heat and light and which contains a specific azo compound excellent in the carrier-generating ability.

It is another object of the present invention to provide an electrophotographic photoreceptor which has a high speed and a small residual electric potential and which is excellent in the durability; that is, even when used repeatedly, the above characteristics are not changed.

It is a further object of the present invention to provide an electrophotographic photoreceptor which contains a azo compound capable of effectively acting as the carrier-generating material even in a combination thereof with any of a large variety of carrier-transport materials.

It is still another object of the present invention to provide a photoreceptor having an adequate sensitivity for practical use even to a long-wavelength light source such as a semiconductor laser.

A still further object of the present invention will be apparent from what are described hereinafter.

As a result of our investigation to attain the above objects, it has now been found that those azo compounds having the following Formula [I] are capable of acting as the excellently effective component of the photoreceptor, and thus the present invention has been accomplished.

Formula [I]

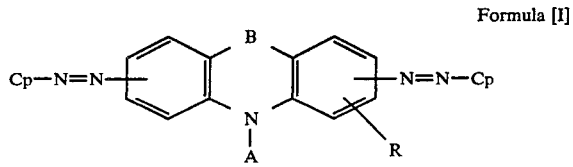

wherein A is a substituted or unsubstituted alkyl group (such as ethyl, propyl, pentyl, methoxyethyl, hydroxyethyl, benzyl, phenethyl, etc.) or a substituted or unsubstituted aryl group (such as phenyl, p-methylphenyl, 2,4-dimethylphenyl, chlorophenyl,

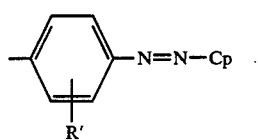

etc.); B is oxygen or sulfur; R and R' each is a hydrogen atom, an alkyl group (such as methyl, ethyl, etc.), an alkoxy group (such as methoxy, ethoxy, etc.), or a halogen atom (such as fluorine, chlorine, bromine); and Cp represents

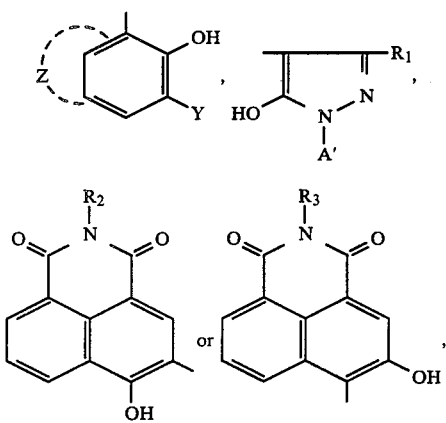

wherein Y is a substituted or unsubstituted carbamoyl group

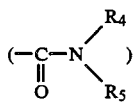

or a substituted or unsubstituted sulfamoyl group

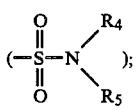

$R_4$ is a hydrogen atom, a substituted or unsubstituted alkyl group having from 1 to 4 carbon atoms, a substituted or unsubstituted aralkyl group, or a substituted or unsubstituted phenyl group; and $R_5$ is a hydrogen atom, a substituted or unsubstituted alkyl group having from 1 to 4 carbon atoms, a substituted or unsubstituted aromatic carbocyclic group (such as substituted or unsubstituted phenyl, substituted or unsubstituted naphthyl, substituted or unsubstituted anthryl, etc.) or a substituted or unsubstituted aromatic heterocyclic group (such as substituted or unsubstituted carbazolyl, substituted or unsubstituted dibenzofuryl, etc.).

The substituent to each of these groups includes, for example, substituted or unsubstituted alkyl groups having from 1 to 4 carbon atoms (such as methyl, ethyl, isopropyl, tertiary butyl, trifluoromethyl, etc.), substituted or unsubstituted aralkyl groups (such as benzyl, phenethyl, etc.), halogen atoms (chlorine, bromine, fluorine, iodine), substituted or unsubstituted alkoxy groups having from 1 to 4 carbon atoms (such as methoxy, ethoxy, isopropoxy, tertiary butoxy, 2-chlorethoxy, etc.), hydroxy group, substituted or unsubstituted aryloxy groups (such as p-chlorophenoxy, 1-naphthoxy, etc.), acyloxy groups (such as acetyloxy, p-cyanobenzoyloxy, etc.), carboxy group and esters thereof (such as ethoxycarbonyl, m-bromophenoxycarbonyl, etc.), carbamoyl groups (such as aminocarbonyl, tertiary butylaminocarbonyl, anilinocarbonyl, etc.), acyl groups (such as acetyl, o-nitrobenzoyl, etc.), sulfo group, sulfamoyl groups (such as aminosulfonyl, tertiary butylaminosulfonyl, p-tolylaminosulfonyl, etc.), amino group, acylamino groups (such as acetylamino, benzoylamino, etc.), sulfonamido groups (such as methanesulfonamido, p-toluenesulfonamido, etc.), cyano group, nitro group, and the like. The preferred substituents among these are the substituted or unsubstituted alkyl group (such as methyl, ethyl, isopropyl, n-butyl, trifluoromethyl, etc.), halogen atom (chlorine, bromine, fluorine, or iodine), substituted or unsubstituted alkoxy group having from 1 to 4 carbon atoms (such as methoxy, ethoxy, tertiary butoxy, 2-chloroethoxy, etc.), cyano group and nitro group.

Z represents a group of atoms necessary to form a substituted or unsubstituted aromatic carbocyclic ring or substituted or unsubstituted aromatic heterocyclic ring, and more particularly, a group of atoms necessary to form, for example, a substituted or unsubstituted benzene ring, substituted or unsubstituted naphthalene ring, substituted or unsubstituted indole ring, substituted or unsubstituted carbazole ring, or the like.

The substituent to a group of atoms which form these rings includes the series of substituents as previously defined in the foregoing $R_4$ and $R_5$, and preferably halogen atoms (chlorine, bromine, fluorine and iodine), sulfo group, sulfamoyl groups (such as aminosulfonyl, p-tolylaminosulfonyl, etc.), and the like.

$R_1$ represents a hydrogen atom, a substituted or unsubstituted alkyl group, a substituted or unsubstituted amino group, a carboxy group or an ester thereof, a substituted or unsubstituted carbamoyl group, or a cyano group, and preferably a hydrogen atom, a substituted or unsubstituted alkyl group having from 1 to 4 carbon atoms (such as methyl, ethyl, tertiary butyl, trifluoromethyl, etc.), or a cyano group.

A' represents a substituted or unsubstituted aryl group, and preferably a substituted or unsubstituted phenyl group. The substituent to the group includes, for example, the series of substituents as defined in the foregoing $R_4$ and $R_5$, and preferably halogen atoms (chlorine, bromine, fluorine and iodine), substituted or unsubstituted alkyl groups having from 1 to 4 carbon atoms (such as methyl, ethyl, isopropyl, tertiary butyl, trifluoromethyl, etc.), substituted or unsubstituted alkoxy groups having from 1 to 4 carbon atoms (such as methoxy, ethoxy, isopropoxy, tertiary butoxy, 2-chloroethoxy, etc.).

$R_2$ and $R_3$ each represents a substituted or unsubstituted alkyl group, a substituted or unsubstituted aralkyl group, or a substituted or unsubstituted aryl group, and preferably a substituted or unsubstituted alkyl group having from 1 to 4 carbon atoms (such as methyl, ethyl, isopropyl, tertiary butyl, trifluoromethyl, etc.), or a substituted or unsubstituted phenyl group (such as phenyl, p-methoxyphenyl, m-chlorophenyl, etc.).

That is, in the present invention, the use of any of those azo compounds having Formula [I] as the photoconductive material constituting the photosensitive layer of a photoreceptor enables to produce an excellent photoreceptor which, as described in the objects of the invention, is stable to heat and light; excellent in the electrophotographic characteristics such as the charge-holding ability, speed, residual electric potential, and the like; little deteriorated even when used repeatedly; and sufficiently sensitive even to longer wavelength regions than 780 nm.

DESCRIPTION OF THE PREFERRED EMBODIMENTS

Figure 1:
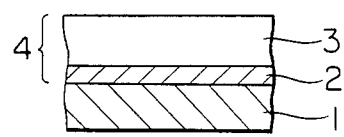
FIGS. 1 to 6 are cross-sectional views showing examples of the mechanical construction of the electrophotographic photoreceptor of the present invention.

The preferred among these bisazo compounds having Formula [I], used in the present invention, are those having the following general formulas [II] through [IX]:

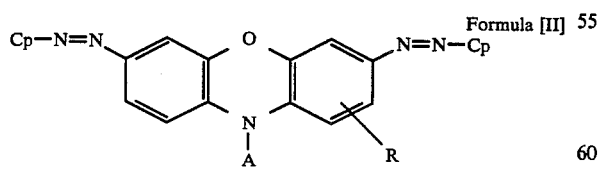
Formula [II]

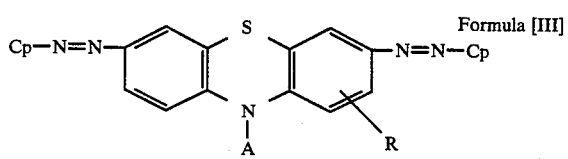
Formula [III]

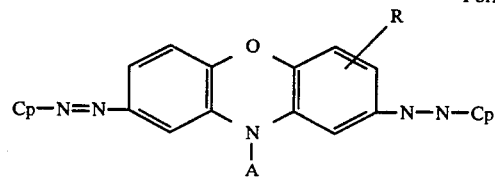
Formula [IV]

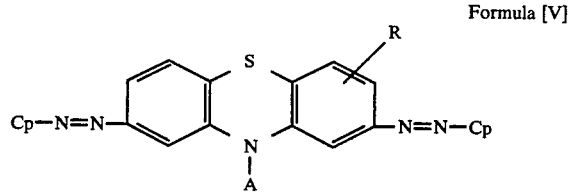
Formula [V]

Especially, as the case that A is represented by

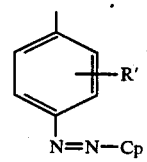

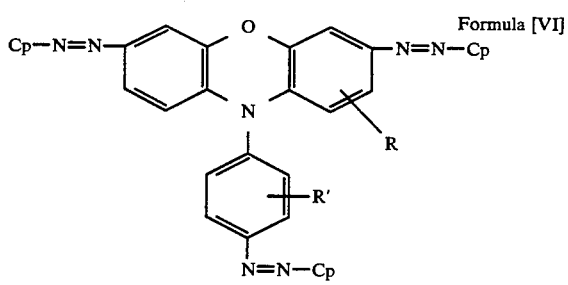
Formula [VI]

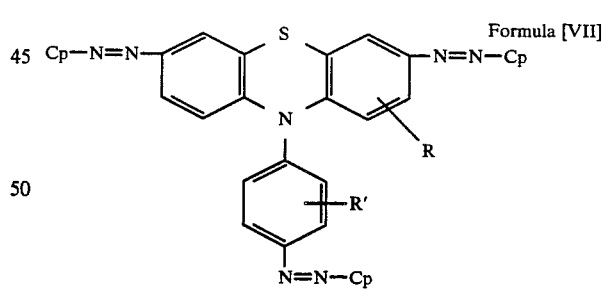
Formula [VII]

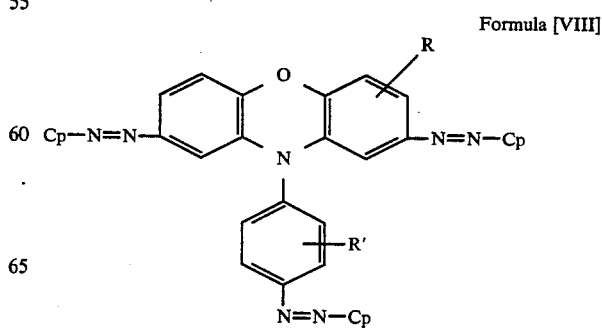
Formula [VIII]

-continued

Formula [IX]
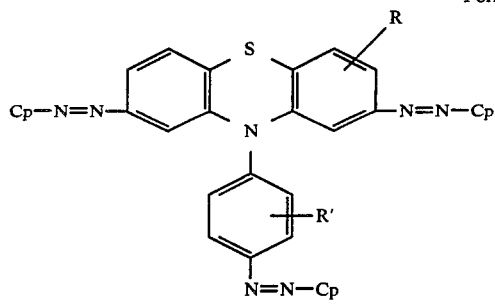

Inter alia, the particularly preferable ones are those having the following Formulae [II'] to [IX'], in which R and R' are hydrogen, H.

Formula [II']
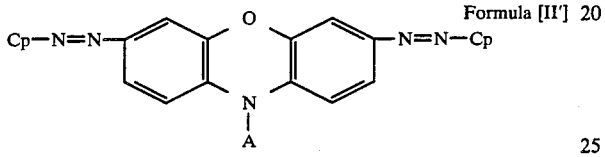

Formula [III']
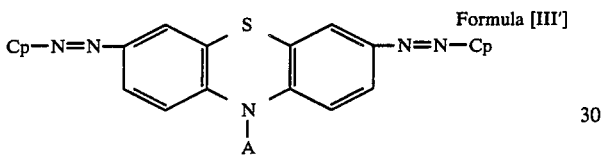

Formula [IV']
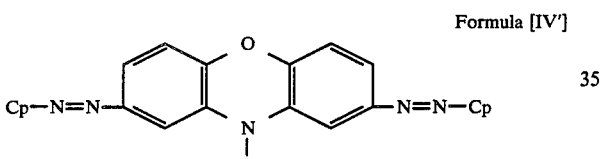

Formula [V']
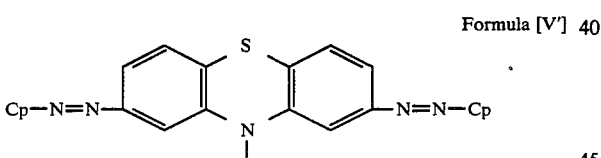

Formula [VI']
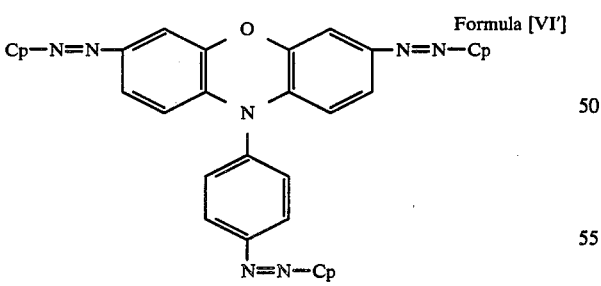

Formula [VII']
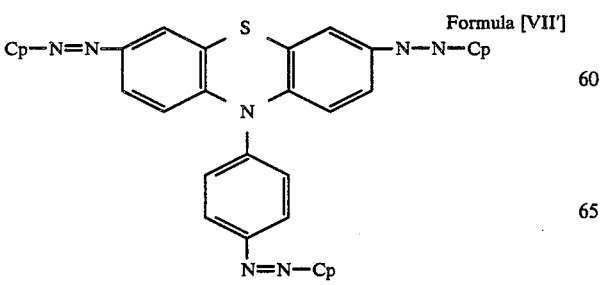

-continued

Formula [VIII']
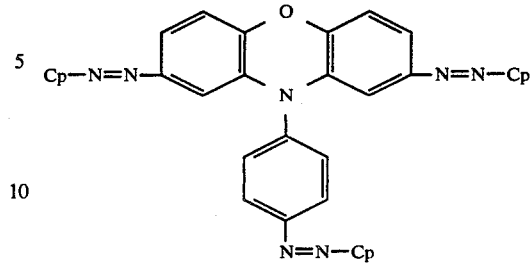

Formula [IX']

Examples of those azo compounds useful in the present invention having the foregoing Formulas [II] through [IX'] are shown in the following table, but the azo compounds of the invention are not limited thereto.

The numerals indicated in the following Formula and Table represent the combined positions of the substituents represented by R or R', respectively.

(1) The compounds having Formula [II];

TABLE (A-1)

Formula [II]

| Compound No. | Cp | R | A |
|---|---|---|---|
| A-(1) | (HO, CONH-aryl-3-CH₃, H₃C, HN-) | 3-CH₃ | —phenyl |
| A-(2) | (HO, CONH-aryl, CH₃) | 3-CH₃ | —C₂H₅ |
| A-(3) | (HO, CONH-aryl, OCH₃) | 3-CH₃ | —phenyl |

Especially, as the compounds having Formula [II'];

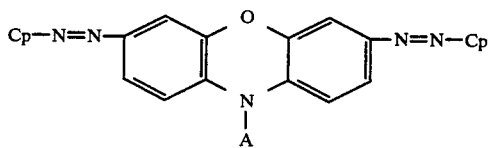
Formula [II']
| Compound No. | Cp | A |
|---|---|---|
| A-(4) | | —C₂H₅ |
| A-(5) | | —C₂H₅ |
| A-(6) | | <br>—⟨benzene⟩—CH₃ |
| A-(7) | | —C₂H₅ |

-continued
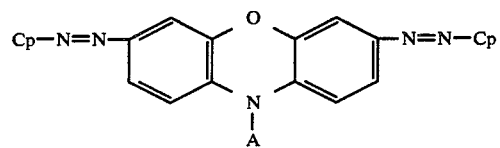
Formula [II']
| Compound No. | Cp | A |
|---|---|---|
| A-(8) | [naphthol with HO, CONH-(2-methyl-4-methylphenyl), CH₃, and HN-phenyl substituents fused structure] | —$\langle$—OCH$_3$ (p-methoxyphenyl) |
| A-(9) | [3-hydroxy-4-methyl-2-naphthanilide] | —C$_2$H$_5$ |
| A-(10) | [3-hydroxy-4-methyl-N-(2,4-dimethylphenyl)-2-naphthamide] | —C$_2$H$_5$ |
| A-(11) | [3-hydroxy-4-methyl-N-(4-methoxyphenyl)-2-naphthamide] | —C$_2$H$_5$ |
| A-(12) | [3-hydroxy-4-methyl-2-naphthanilide] | —phenyl |

-continued
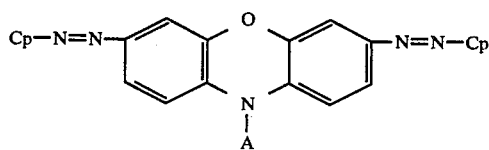
Formula [II']
| Compound No. | Cp | A |
|---|---|---|
| A-(13) | 3-hydroxy-4-methyl-N-(2,5-dimethoxyphenyl)-2-naphthamide | phenyl |
| A-(14) | 3-hydroxy-4-methyl-N-(4-chlorophenyl)-2-naphthamide | —C$_2$H$_5$ |
| A-(15) | 3-hydroxy-4-methyl-N-(2-chloro-4,5-dimethoxyphenyl)-2-naphthamide | —C$_2$H$_5$ |
| A-(16) | 3-hydroxy-4-methyl-N-(4-chloro-2-methylphenyl)-2-naphthamide | 4-methylphenyl |
| A-(17) | 3-hydroxy-4-methyl-N-(3-nitrophenyl)-2-naphthamide | phenyl |

-continued
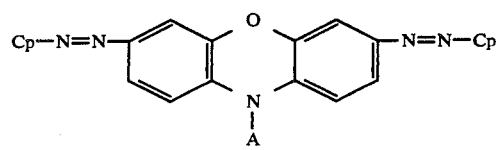 Formula [II']
| Compound No. | Cp | A |
|---|---|---|
| A-(18) | 3-hydroxy-N-(2,4-dimethylphenyl)-4-methyl-2-naphthamide | phenyl |
| A-(19) | 3-hydroxy-N-(2-naphthyl)-2-naphthamide | —C₃H₇(n) |
| A-(20) | 3-hydroxy-N-(1-naphthyl)-4-methyl-2-naphthamide | —C₃H₇(n) |
| A-(21) | 3-hydroxy-N-(4-methoxyphenyl)-4-methyl-2-naphthamide | phenyl |
| A-(22) | 3-hydroxy-N-(2-methoxy-4-phenoxyphenyl)-4-methyl-2-naphthamide | —C₂H₅ |

-continued

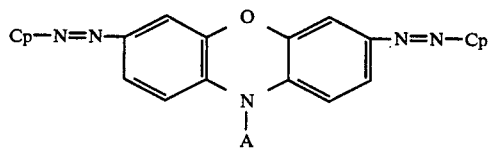 Formula [II']

| Compound No. | Cp | A |
|---|---|---|
| A-(23) | (3-hydroxy-1-methyl-2-naphthanilide fused with anthracene, N-(2-methylphenyl)) | —C$_2$H$_5$ |
| A-(24) | 3-hydroxy-1-methyl-N-(4-chloro-2,5-dimethoxyphenyl)-2-naphthamide | —C$_6$H$_4$—CH$_3$ (p-tolyl) |
| A-(25) | 3-hydroxy-1-methyl-N-(2,5-dimethoxyphenyl)-2-naphthamide with dibenzofuran substituent | —C$_2$H$_5$ |
| A-(26) | 3-hydroxy-1-methyl-N-(4-chlorophenyl)-2-naphthamide with carbazole substituent | —C$_2$H$_5$ |

-continued
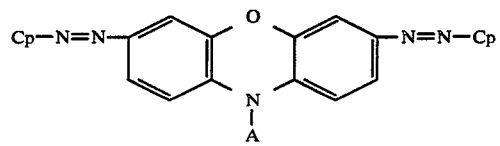 Formula [II']
| Compound No. | Cp | A |
|---|---|---|
| A-(27) | 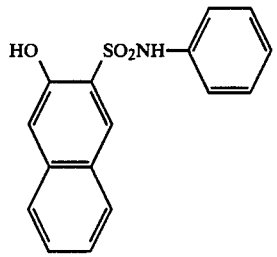 | —C$_2$H$_5$ |
| A-(28) | 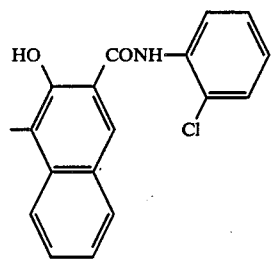 | —C$_2$H$_5$ |
| A-(29) | 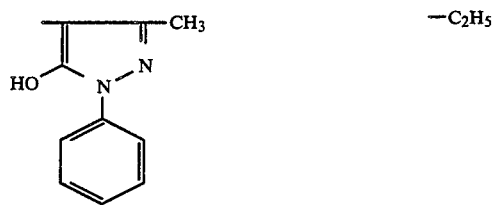 | —C$_2$H$_5$ |
| A-(30) | 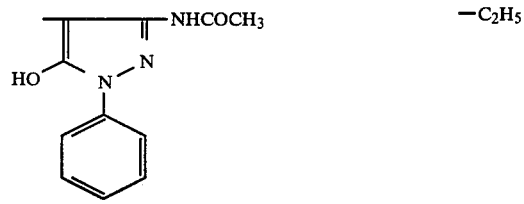 | —C$_2$H$_5$ |
| A-(31) | 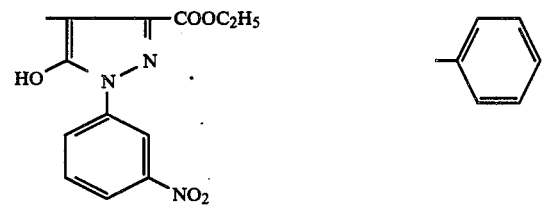 | 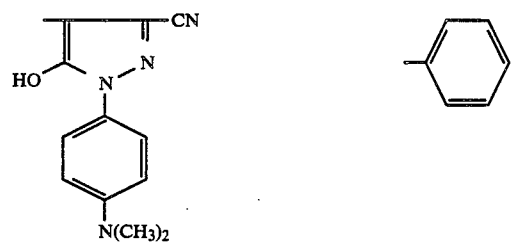 |
| A-(32) | 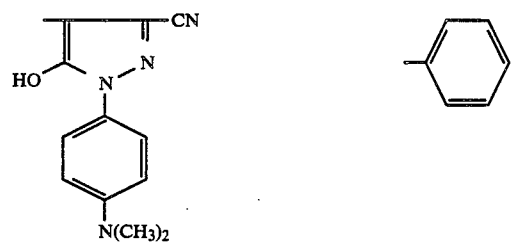 | |

-continued
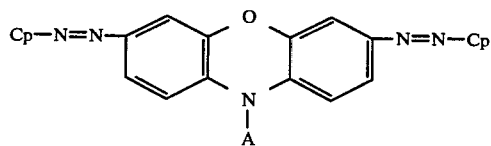
Formula [II']
| Compound No. | Cp | A |
|---|---|---|
| A-(33) | (N-ethyl naphthalimide with OH and CH3) | —C$_2$H$_5$ |
| A-(34) | (N-phenyl naphthalimide with OH and CH3) | —C$_2$H$_5$ |
| A-(35) | (N-benzyl naphthalimide with OH and CH3) | (p-tolyl, —CH$_3$) |
| A-(36) | (N-methyl naphthalimide with OH and CH3) | (p-methoxyphenyl, —OCH$_3$) |
| A-(37) | (N-(CH$_2$CH$_2$CH$_2$OCH$_3$) naphthalimide with OH and CH3) | —C$_2$H$_5$ |

Formula [II']

| Compound No. | Cp | A |
|---|---|---|
| A-(38) | 4-nitrophenyl-naphthalimide with OH and CH₃ | —C₂H₅ |
| A-(39) | 4-methoxybenzyl-naphthalimide with OH and CH₃ | p-tolyl (—C₆H₄—CH₃) |

(2) The compounds having Formula [III];

TABLE (A-2)

Formula [III]

| Compound No. | Cp | R | A |
|---|---|---|---|
| A-(40) | 3-hydroxy-4-methyl-N-(2-methylphenyl)-2-naphthamide | 3-CH₃ | —C₂H₄OCH₃ |
| A-(41) | 3-hydroxy-4-methyl-N-(2-naphthyl)-2-naphthamide | 3-CH₃ | —C₂H₅ |

Especially, as the compounds having Formula [III];

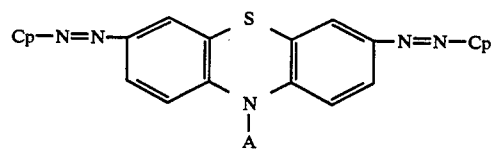
| Compound No. | Cp | A |
|---|---|---|
| A-(42) | 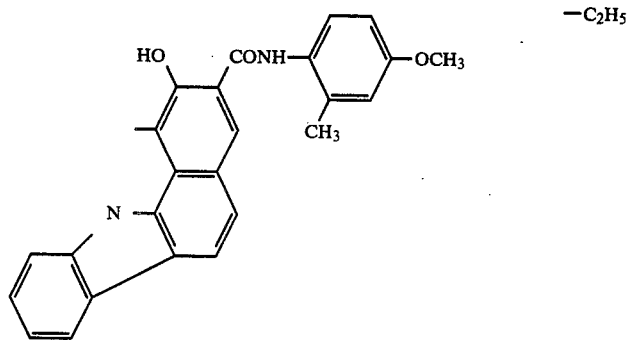 | —C$_2$H$_5$ |
| A-(43) | 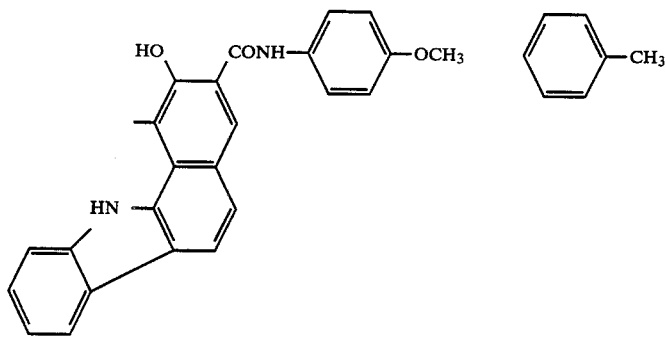 | —CH$_3$ |
| A-(44) | 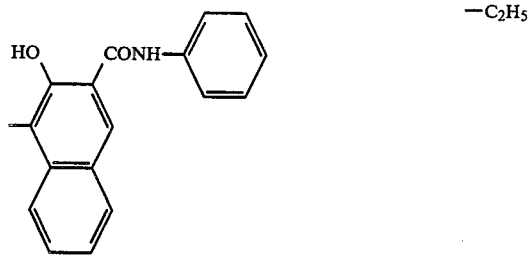 | —C$_2$H$_5$ |
| A-(45) | 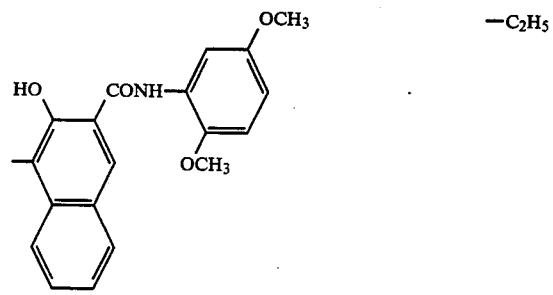 | —C$_2$H$_5$ |

-continued
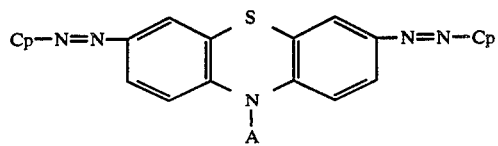
| Compound No. | Cp | A |
|---|---|---|
| A-(46) | 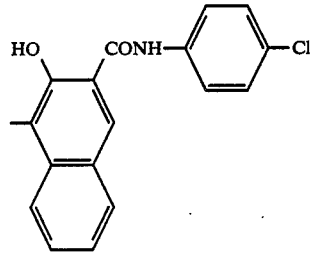 | —C$_3$H$_7$(n) |
| A-(47) | 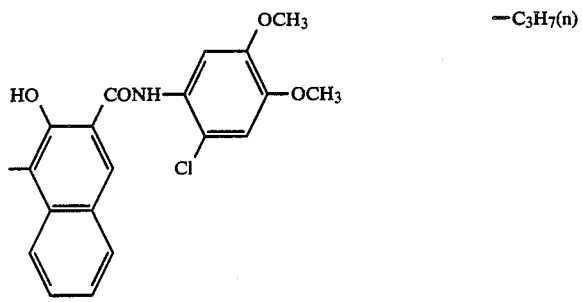 | —C$_3$H$_7$(n) |
| A-(48) | 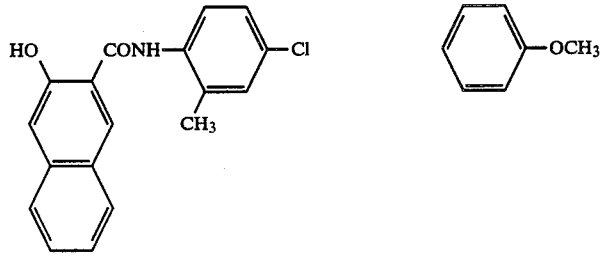 | 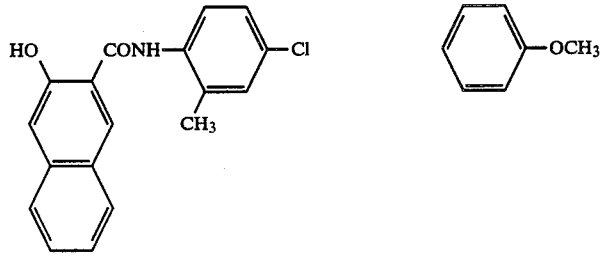 |
| A-(49) | 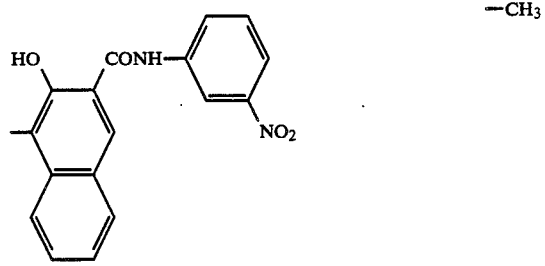 | —CH$_3$ |
| A-(50) | 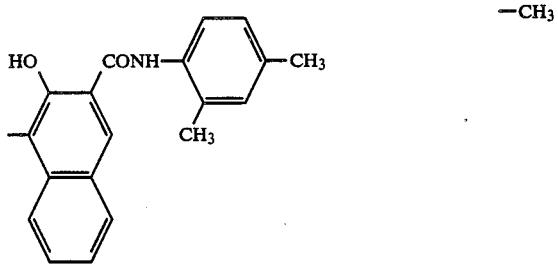 | —CH$_3$ |

-continued
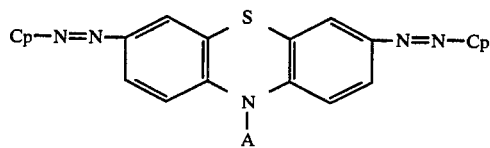
| Compound No. | Cp | A |
|---|---|---|
| A-(51) | [3-hydroxy-4-methyl-N-(2-methoxyphenyl)-2-naphthamide] | $-C_2H_4OCH_3$ |
| A-(52) | [3-hydroxy-4-methyl-N-(1-naphthyl)-2-naphthamide] | $-C_2H_5$ |
| A-(53) | [3-hydroxy-4-methyl-N-(4-methoxyphenyl)-2-naphthamide] | $-C_3H_7(n)$ |
| A-(54) | [3-hydroxy-4-methyl-N-(2-methoxy-5-phenoxyphenyl)-2-naphthamide] | $-C_3H_7(n)$ |
| A-(55) | [3-hydroxy-4-methyl-N-(2-methylphenyl)-2-anthramide] | $-C_2H_5$ |

-continued
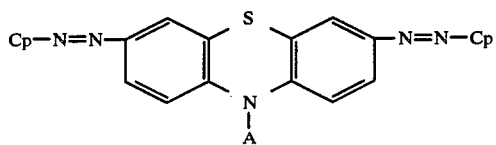
| Compound No. | Cp | A |
|---|---|---|
| A-(56) | 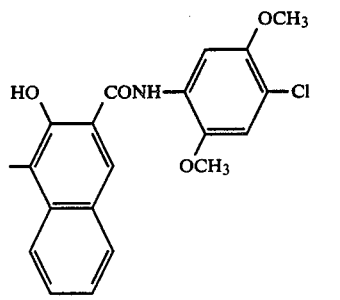 | 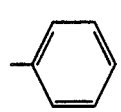 |
| A-(57) | 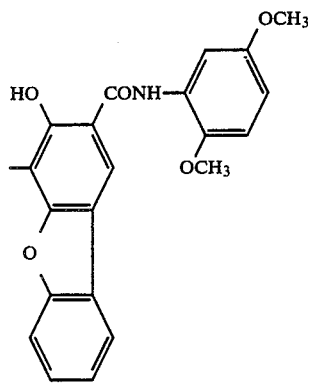 | 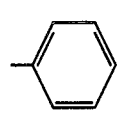 |
| A-(58) | 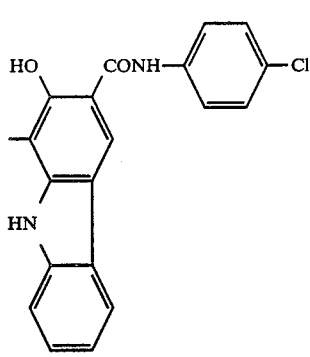 | 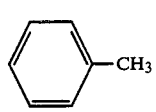 |
| A-(59) | 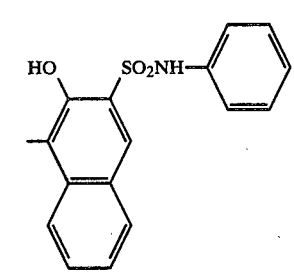 | —$C_2H_5$ |

-continued
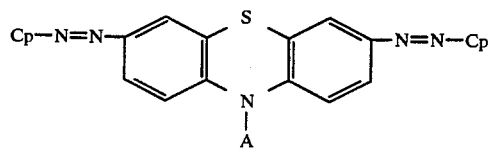
| Compound No. | Cp | A |
|---|---|---|
| A-(60) | (3-hydroxy-4-methyl-N-(2-chlorophenyl)-2-naphthamide) | —C$_3$H$_7$(n) |
| A-(61) | (3-methyl-1-phenyl-5-hydroxypyrazole) | —C$_2$H$_5$ |
| A-(62) | (3-acetamido-1-phenyl-5-hydroxypyrazole) | —C$_2$H$_5$ |
| A-(63) | (3-carboxy-1-phenyl-5-hydroxypyrazole) | —C$_2$H$_5$ |
| A-(64) | (3-ethoxycarbonyl-1-(3-nitrophenyl)-5-hydroxypyrazole) | —C$_3$H$_7$(n) |
| A-(65) | (3-cyano-1-(4-dimethylaminophenyl)-5-hydroxypyrazole) | —C$_3$H$_7$(n) |

-continued
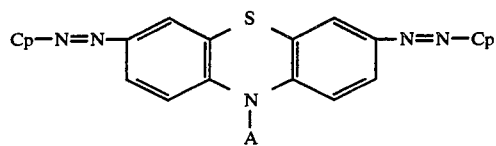
| Compound No. | Cp | A |
|---|---|---|
| A-(66) | (N-ethyl naphthalimide with OH and CH3) | —C$_2$H$_4$OCH$_3$ |
| A-(67) | (N-phenyl naphthalimide with OH and CH3) | —C$_2$H$_5$ |
| A-(68) | (N-benzyl naphthalimide with OH and CH3) | —C$_3$H$_7$(n) |
| A-(69) | (N-methyl naphthalimide with OH and CH3) | (phenyl) |
| A-(70) | (N-(CH$_2$CH$_2$CH$_2$OCH$_3$) naphthalimide with OH) | (phenyl) |

-continued
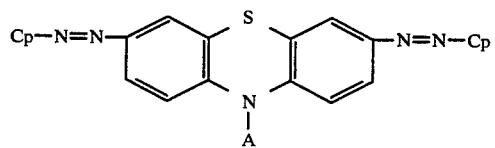
| Compound No. | Cp | A |
|---|---|---|
| A-(71) | 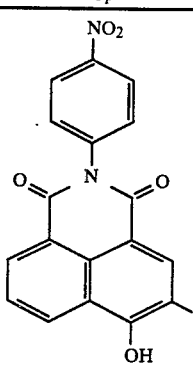 | —C$_3$H$_7$(n) |
| A-(72) | 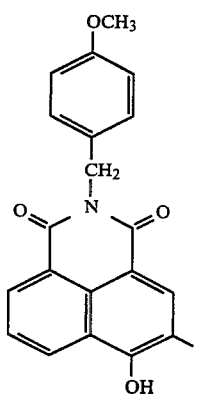 | —C$_2$H$_5$ |
(3) The compounds having Formula [IV];
TABLE (A-3)
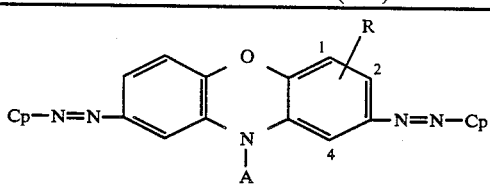  Formula [IV]
| | Cp | R | A |
|---|---|---|---|
| A-(73) | 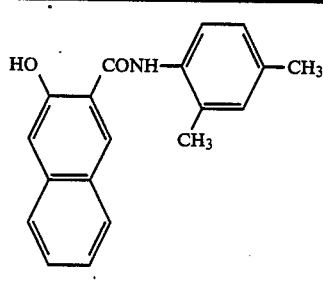 | 1-CH$_3$ | —C$_2$H$_5$ |

TABLE (A-3)-continued

Formula [IV]

| | Cp | R | A |
|---|---|---|---|
| A-(74) | HO, CONH–C₆H₄–Br (3-hydroxy-4-methyl-2-naphthamide with 4-bromoanilide) | 2-Cl | –C₆H₄–CH₃ (p-tolyl) |
| A-(75) | HO, CONH–C₆H₄–OCH₃ (3-hydroxy-methyl naphthamide with 4-methoxyanilide, fused HN-phenyl) | 2-Cl | –C₂H₅ |
| A-(76) | HO, CONH–C₆H₄–Cl (3-hydroxy-methyl naphthamide with 2-chloroanilide, fused HN-phenyl) | 1-OCH₃ | –C₆H₄–CH₃ (p-tolyl) |

Especially, as the compounds having Formula [IV'];

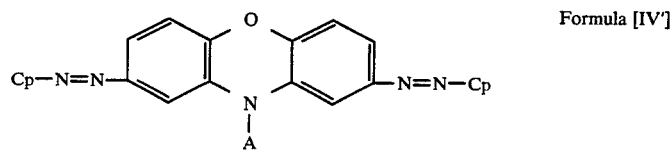
Formula [IV']
| Compound No. | Cp | A |
|---|---|---|
| A-(77) | 3-hydroxy-N-phenyl-naphthalene-2-carboxamide (with CH₃ at position 4) | —C₂H₅ |
| A-(78) | 3-hydroxy-N-(2-methylphenyl)-naphthalene-2-carboxamide (with CH₃) | —C₃H₇(n) |
| A-(79) | 3-hydroxy-N-(2,4-dimethylphenyl)-naphthalene-2-carboxamide (with CH₃) | 4-methylphenyl (—C₆H₄—CH₃) |
| A-(80) | hydroxy-carboxamide fused carbazole derivative with 2-C₂H₅-phenyl | —C₂H₅ |
(4) The compounds having Formula [V];

TABLE (A-4)

Formula [V]

[Structure: Cp—N=N— phenothiazine core with S bridge, N-A, positions 1,2,4 and R substituent, —N=N—Cp]

| Compound No. | Cp | R | A |
|---|---|---|---|
| A-(81) | [3-hydroxy-4-methyl-naphthalene-2-carboxamide with N-(2-methylphenyl)] | 1-OCH$_3$ | —CH$_3$ |
| A-(82) | [3-hydroxy-4-methyl-naphthalene-2-carboxamide with N-(2-chlorophenyl)] | 2-CH$_3$ | [phenyl] |
| A-(83) | [fused benz[a]carbazole hydroxy carboxamide with N-(4-methoxy-2-methylphenyl)] | 1-CH$_3$ | —CH$_3$ |
| A-(84) | [fused benz[a]carbazole hydroxy carboxamide with N-(3-nitrophenyl)] | 1-Cl | [phenyl] |

Especially, as the compounds having Formula [V'];

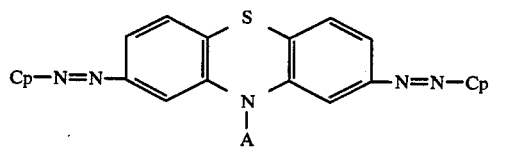
Formula [V']
| Compound No. | Cp | A |
|---|---|---|
| A-(85) | [3-hydroxy-4-methyl-N-phenyl-2-naphthamide] | —C$_2$H$_5$ |
| A-(86) | [3-hydroxy-4-methyl-N-(4-methylphenyl)-2-naphthamide] | [4-methylphenyl] |
| A-(87) | [3-hydroxy-4-methyl-N-(2,4-dimethylphenyl)-2-naphthamide] | —C$_2$H$_5$ |
| A-(88) | [3-hydroxy-4-methyl-N-(4-methoxyphenyl)-2-naphthamide] | —C$_3$H$_7$(n) |
| A-(89) | [3-hydroxy-4-methyl-N-(4-methoxy-2-methylphenyl)-2-naphthamide] | —C$_2$H$_5$ |

(5) Among the compounds having Formula [VI];
TABLE (A-5)
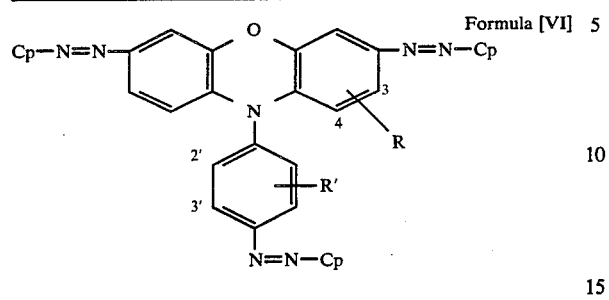
Formula [VI]
| Compound No. | Cp | R | R' |
|---|---|---|---|
| A-(90) | 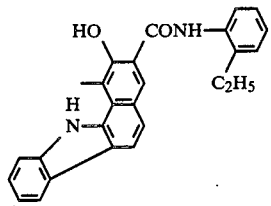 | 3-CH₃ | —H |
| | | | C₂H₅ |
| A-(91) | 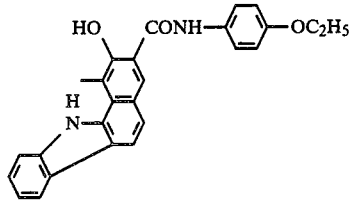 | —H | 3'-C₃H₇ |
| A-(92) | 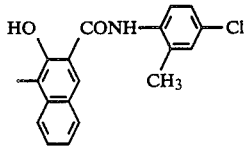 | —H | 3'-CH₃ |
| A-(93) | 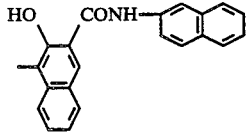 | —H | 3'-CH₃ |
| A-(94) | 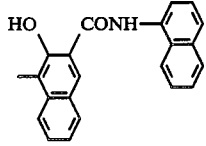 | —H | 3'-CH₃ |
| A-(95) | 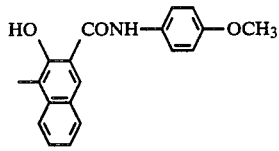 | —H | 3'-CH₃ |
TABLE (A-5)-continued
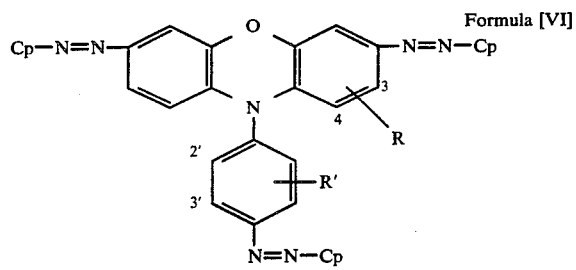
Formula [VI]
| Compound No. | Cp | R | R' |
|---|---|---|---|
| A-(96) | 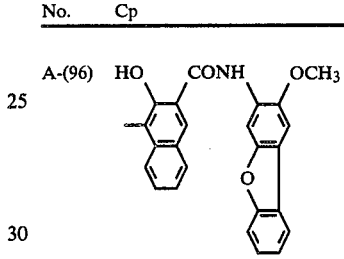 | —H | 3'-OCH₃ |
| A-(97) | 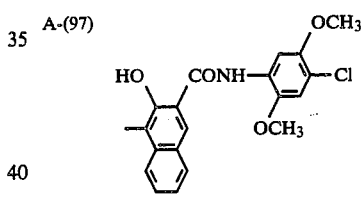 | —H | 3'-OCH₃ |
| A-(98) | 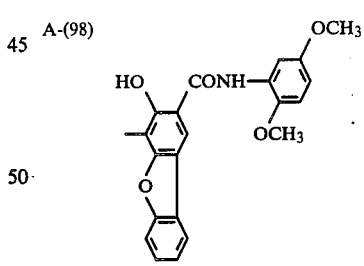 | —H | 3'-CH₃ |
| A-(99) | 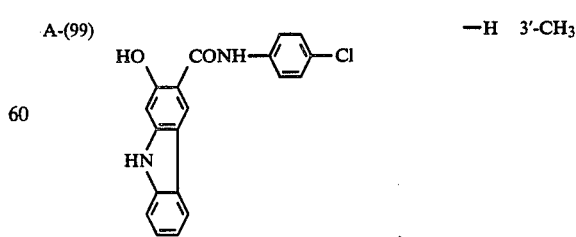 | —H | 3'-CH₃ |
Especially, as the compounds having Formula [VI'];

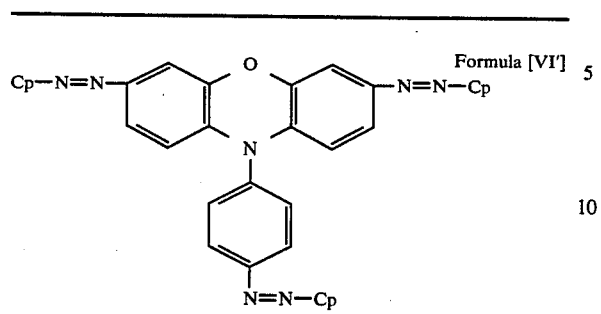
Formula [VI']
Compound No. Cp
A-(100)
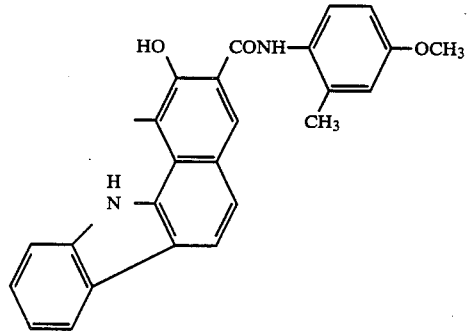
A-(101)
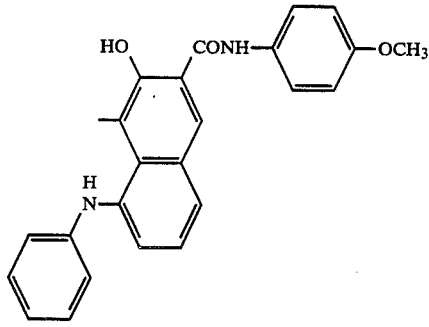
A-(102)
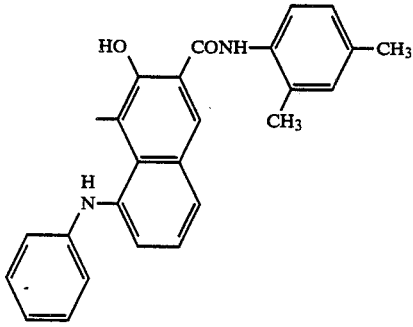
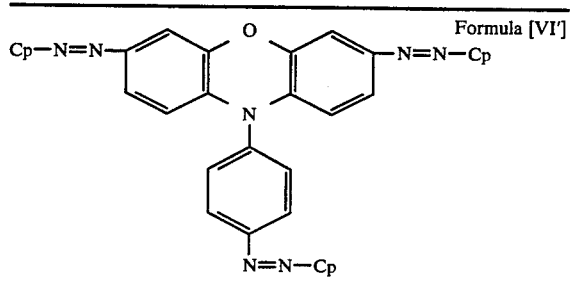
Formula [VI']
Compound No. Cp
A-(103)
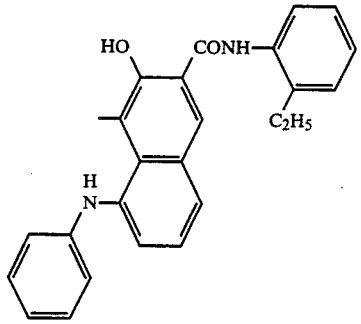
A-(104)
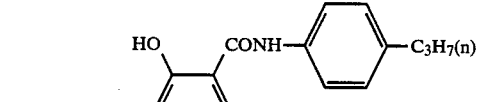
A-(105)
A-(106)

-continued
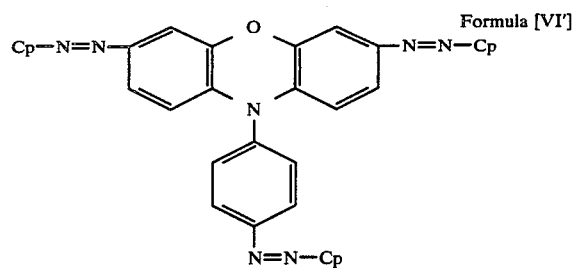
Formula [VI']
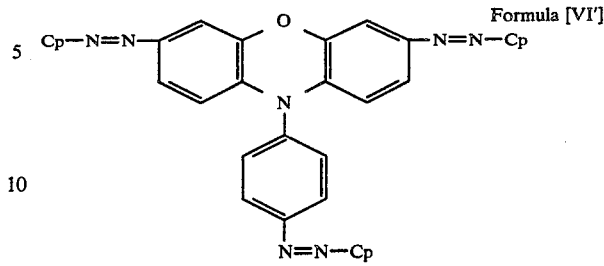
Formula [VI']
| Compound No. | Cp |
|---|---|
| A-(107) | 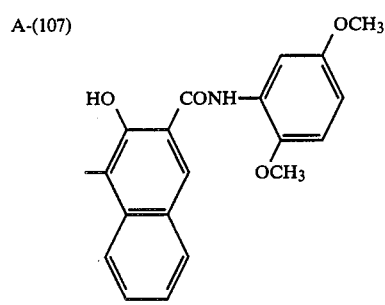 |
| A-(108) | 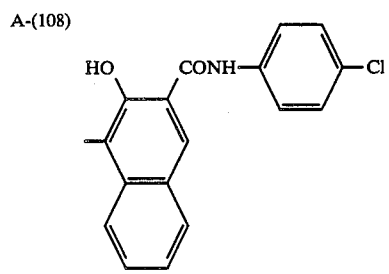 |
| A-(109) | 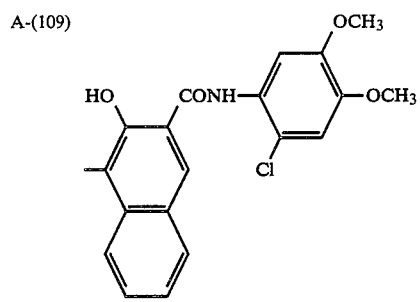 |
| A-(110) | 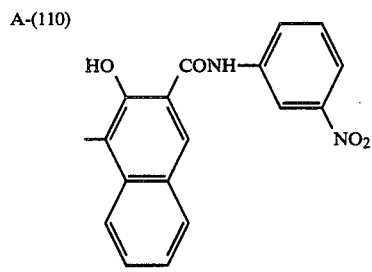 |
| Compound No. | Cp |
|---|---|
| A-(111) | 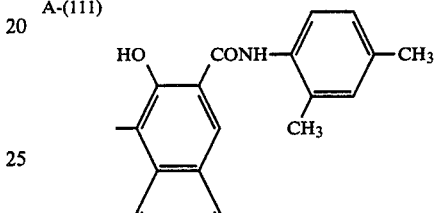 |
| A-(112) | 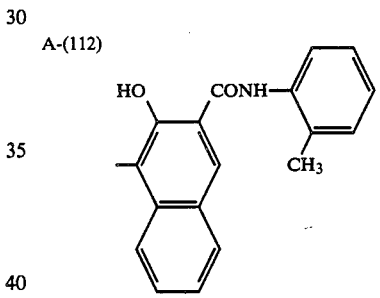 |
| A-(113) | 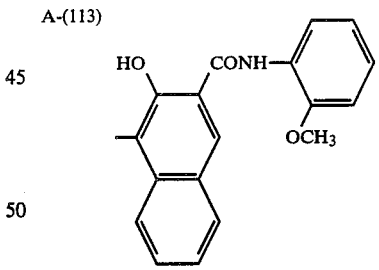 |
| A-(114) | 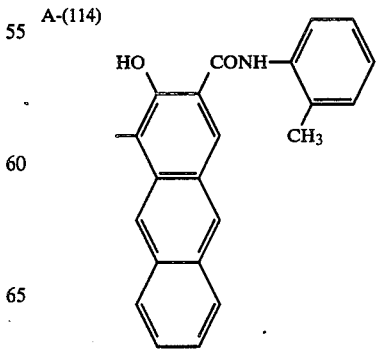 |

-continued
Formula [VI']
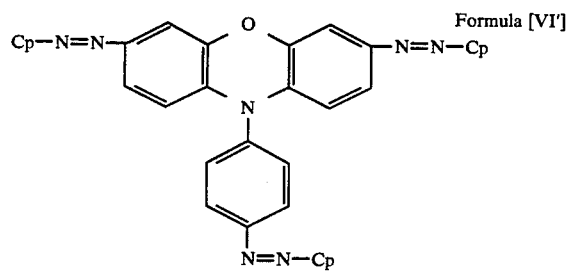
| Compound No. | Cp |
|---|---|
| A-(115) | 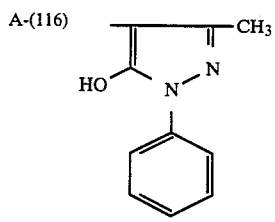 |
| A-(116) | 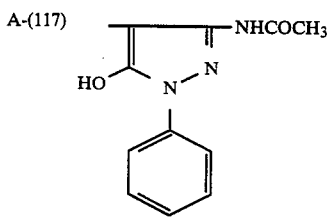 |
| A-(117) | 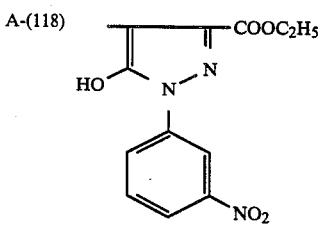 |
| A-(118) | 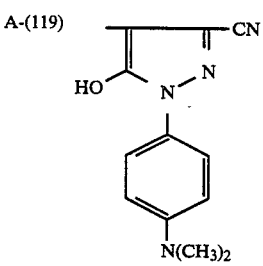 |
| A-(119) | |
-continued
Formula [VI']
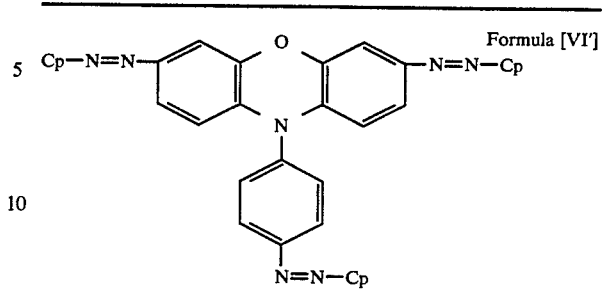
| Compound No. | Cp |
|---|---|
| A-(120) | |
| A-(121) | |
| A-(122) | |
| A-(123) | |

-continued
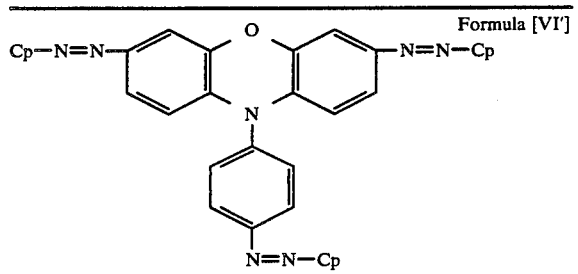
Formula [VI']
| Compound No. | Cp |
|---|---|
| A-(124) | 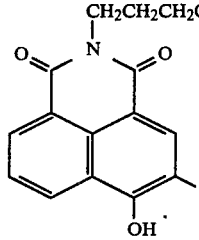 |
| A-(125) | 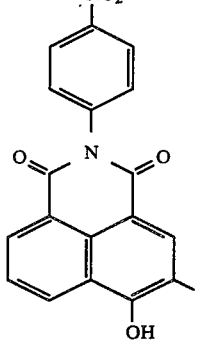 |
-continued
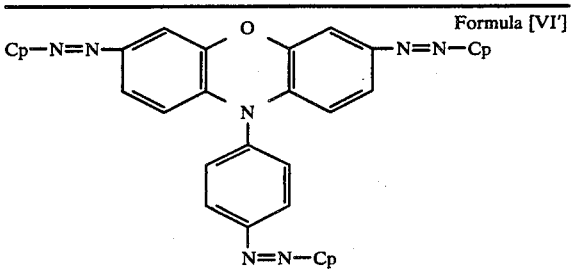
Formula [VI']
| Compound No. | Cp |
|---|---|
| A-(126) | 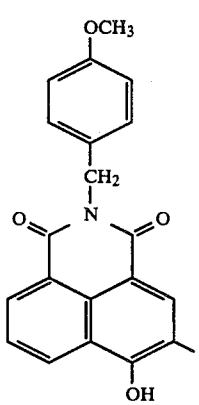 |
(6) The compounds having Formula [VII];
TABLE (A-6)
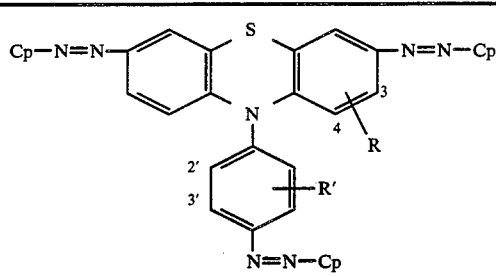
Formula [VII]
| Compound No. | Cp | R | R' |
|---|---|---|---|
| A-(127) | 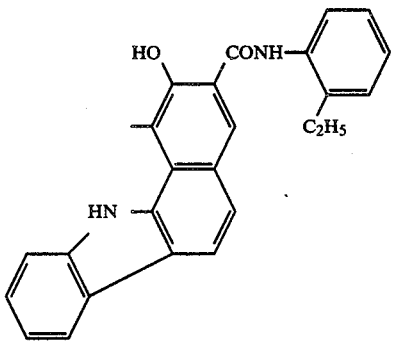 | 3-$CH_3$ | —H |

TABLE (A-6)-continued
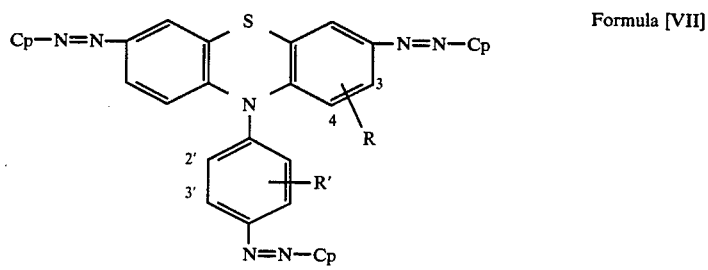
Formula [VII]
| Compound No. | Cp | R | R' |
|---|---|---|---|
| A-(128) | (3-hydroxy-4-methyl-naphthalene with HN-phenyl substituent and CONH-C6H4-OC2H5) | —H | 3'-CH3 |
| A-(129) | (3-hydroxy-4-methyl-2-naphthamide with N-(2-chloro-4,5-dimethoxyphenyl)) | —H | 3'-OCH3 |
| A-(130) | (3-hydroxy-4-methyl-2-naphthamide with N-(3-nitrophenyl)), with Cl on phenyl | —H | 3'-Cl |
| A-(131) | (3-hydroxy-4-methyl-2-naphthamide with N-(2-naphthyl)) | —H | 3'-CH3 |

TABLE (A-6)-continued
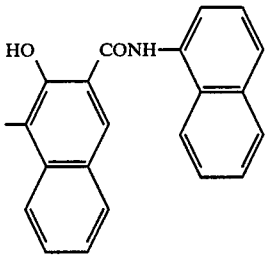
Formula [VII]
| Compound No. | Cp | R | R' |
|---|---|---|---|
| A-(132) | 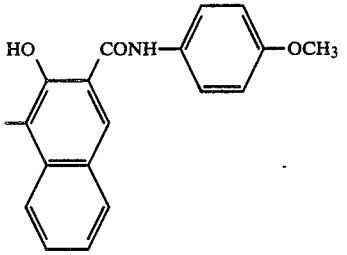 | —H | 3'-CH₃ |
| A-(133) | 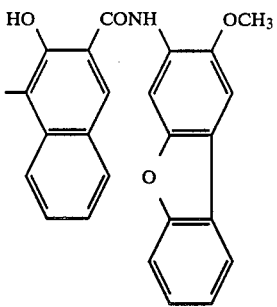 | —H | 3'-CH₃ |
| A-(134) | 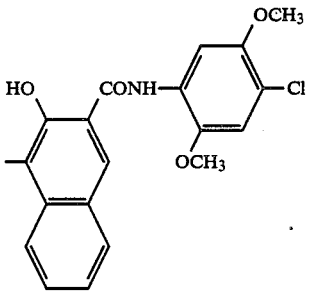 | —H | 3'-OCH₃ |
| A-(135) |  | —H | 3'-OCH₃ |

TABLE (A-6)-continued

Formula [VII]

Compound No. | Cp | R | R'
--- | --- | --- | ---
A-(136) | [structure: 3-hydroxy-N-(4-chlorophenyl)-carboxamide with NH-phenyl substituent] | —H | 3'-CH₃
A-(137) | [structure: 3-hydroxy-2-naphthalenyl SO₂NH-phenyl] | —H | 3'-CH₃

Especially, as the compounds having Formula [VII'];

Formula [VII']

Compound No. | Cp
--- | ---

-continued
A-(138)
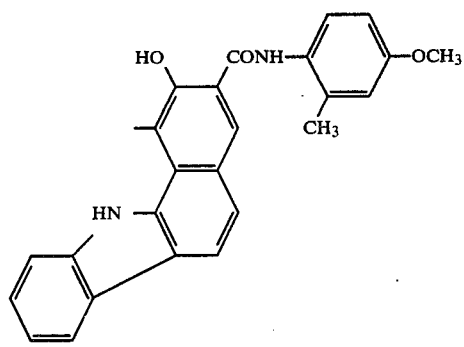
A-(139)
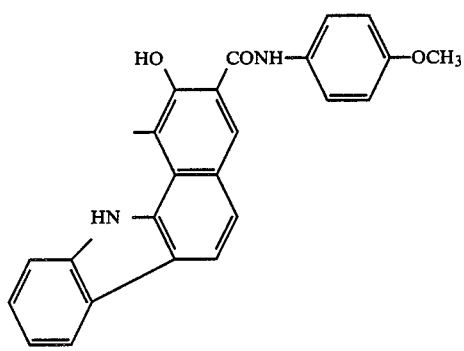
A-(140)
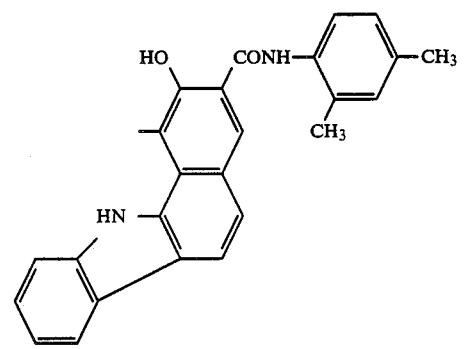
A-(141)
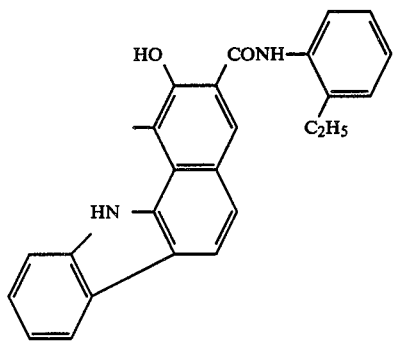

-continued
A-(142)
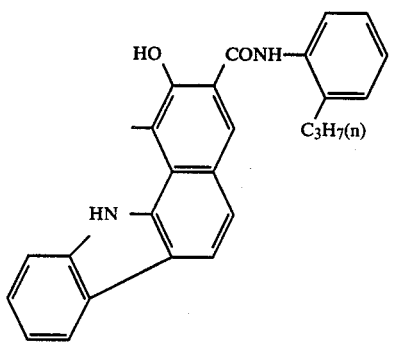
A-(143)
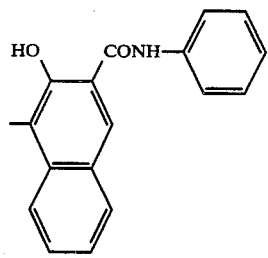
A-(144)
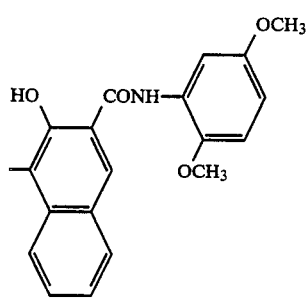
A-(145)
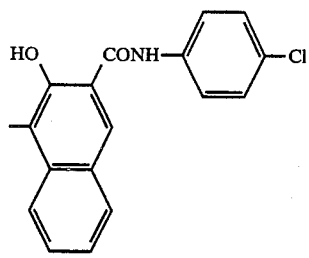
A-(146)
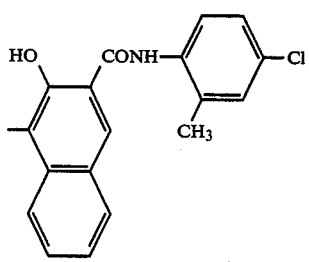

-continued
A-(147)
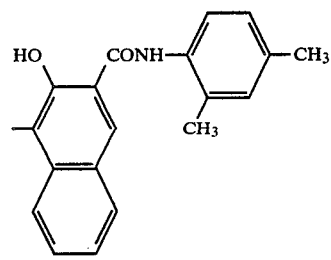
A-(148)
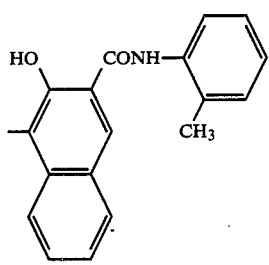
A-(149)
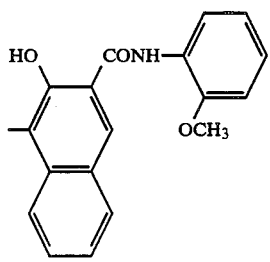
A-(150)
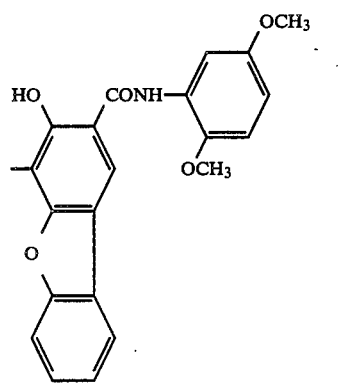

-continued
A-(151)
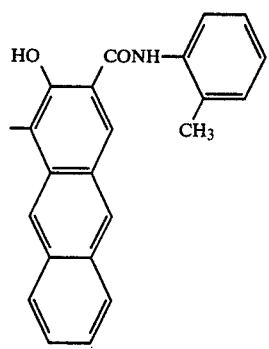
A-(152)
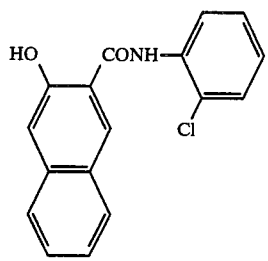
A-(153)
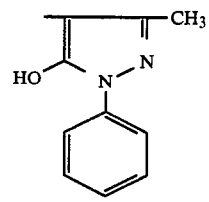
A-(154)
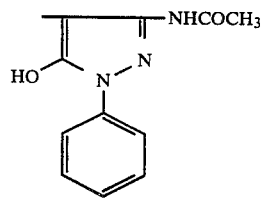
A-(155)
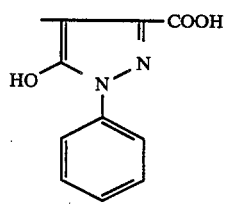
A-(156)
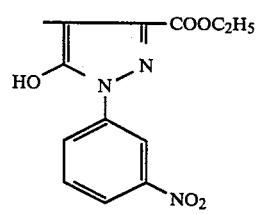

-continued
A-(157) 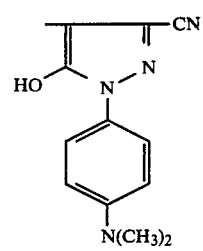
A-(158) 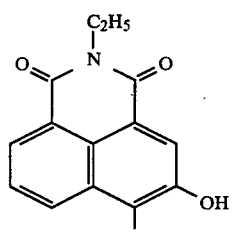
A-(159) 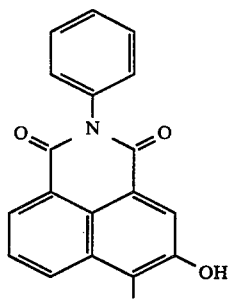
A-(160) 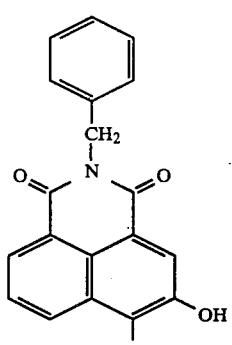
A-(161) 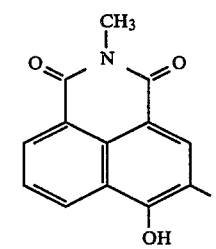

-continued
A-(162) 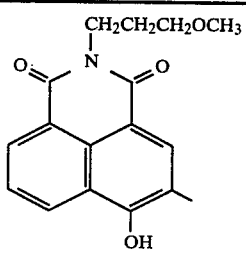
A-(163) 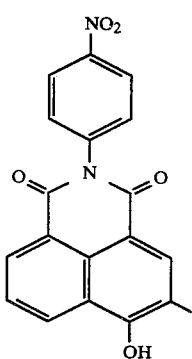
A-(164) 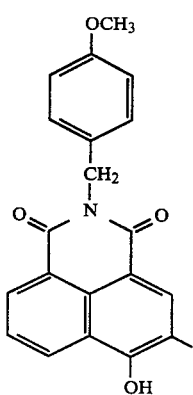
(7) Among the compounds having Formula [VIII];

TABLE (A-7)
Formula [VIII]
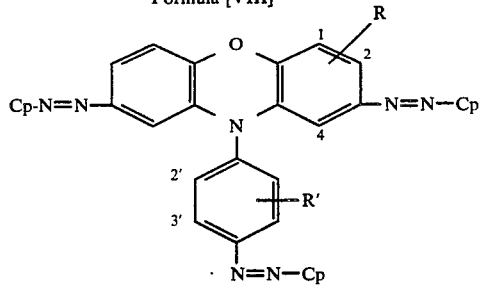
| Compound No. | Cp | R | R' |
|---|---|---|---|
| A-(165) | 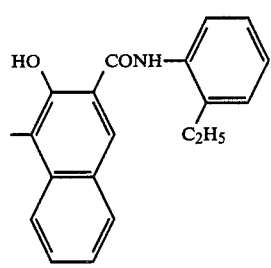 | —H | 3'-CH₃ |
| A-(166) | 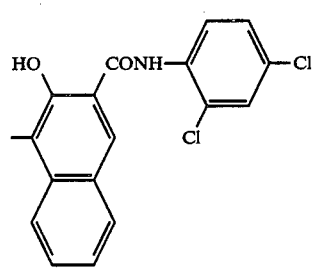 | 2-Cl | 2'-CH₃ |
| A-(167) | 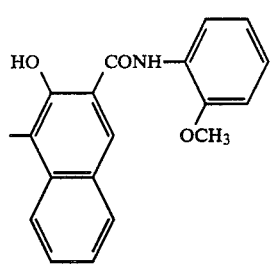 | 1-C₂H₅ | —H |
| A-(168) | 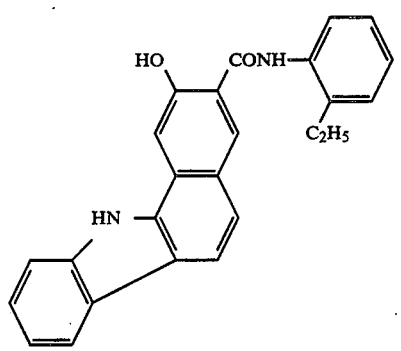 | 2-CH₃ | —H |

TABLE (A-7)-continued

Formula [VIII]

| Compound No. | Cp | R | R' |
|---|---|---|---|
| A-(169) | [structure: 3-hydroxy-N-(4-octylphenyl)-carbamoyl naphthalene fused with carbazole-like HN group] | 2-Br | 2'-CH₃ |

Especially, as the compounds having Formula [VIII'];

Formula [VIII']

| Compound No. | Cp |
|---|---|
| A-(170) | [structure: HO, CONH-phenyl, with CH₃ on naphthalene] |
| A-(171) | [structure: HO, CONH-(2,4-dimethylphenyl), with CH₃ on naphthalene] |
| A-(172) | [structure: HO, CONH-(2-methyl-4-methoxyphenyl), fused naphthalene with HN-carbazole] |

(8) The compounds having Formula [IX];

TABLE (A-8)
Formula [IX]
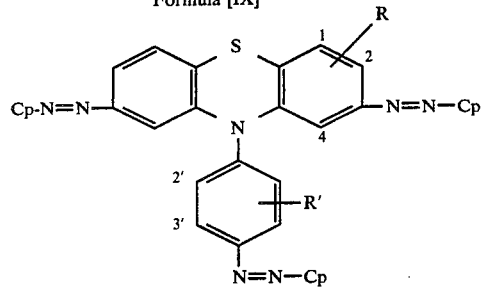
| Compound No. | Cp | R | R' |
|---|---|---|---|
| A-(173) | 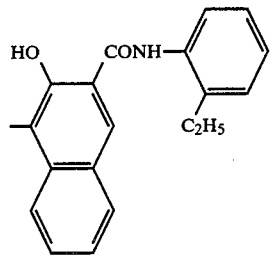 | —H | 3'-CH$_3$ |
| A-(174) | 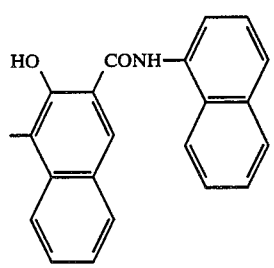 | 1-OCH$_3$ | —H |
| A-(175) | 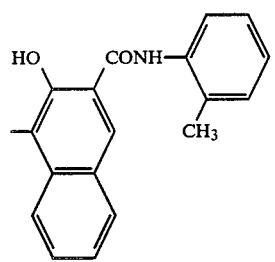 | 1-CH$_3$ | 2'-CH$_3$ |
| A-(176) | 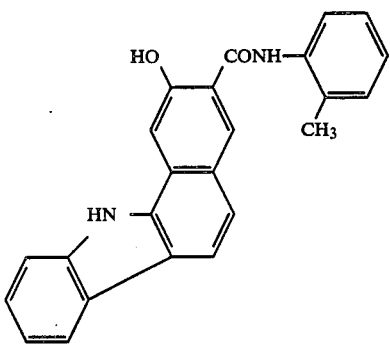 | 1-CH$_3$ | —H |

TABLE (A-8)-continued

| | | | |
|---|---|---|---|
| A-(177) | 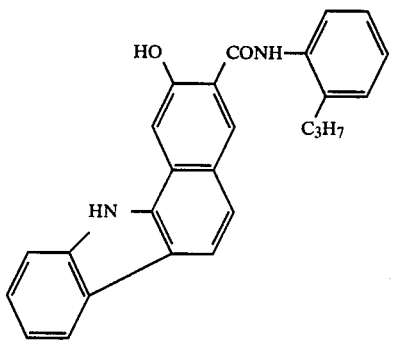 | 2-Cl | 2'-Cl |

Especially, as the compounds having Formula [IX'];

Formula [IX']

Cp-N=N-[structure with S, N, phenyl groups]-N=N-Cp
       |
       N=N-Cp

| Compound No. | Cp |
|---|---|
| A-(178) | HO, CONH-phenyl, naphthalene with CH₃ |
| A-(179) | HO, CONH-phenyl(2,4-diCH₃), naphthalene with CH₃ |

-continued

Formula [IX']

Cp-N=N-[structure with S, N, phenyl groups]-N=N-Cp
       |
       N=N-Cp

| Compound No. | Cp |
|---|---|
| A-(180) | HO, CONH-phenyl(4-OCH₃, 2-CH₃), naphthalene with HN-phenyl |

The azo compound of this invention has an excellent photoconductivity, and when this is used to produce an electrophotographic photoreceptor, the production can be carried out by providing on a conductive support a photosensitive layer comprising a binder into which is dispersed the azo compound of the invention. The production may also be made otherwise: The azo compound of the invention is used as a carrier-generating material, which utilizes the particularly excellent carrier-generating ability as the photoconductivity thereof, and this is used with a carrier-transport material which, when used in combination therewith, is capable of effectively acting, whereby an electrophotographic photoreceptor of the multilayer type or of the dispersion type; i.e., the function-separated type, can be produced. The azo compounds having Formula [I] of the invention can be used alone or in combination of two or more thereof, and can also be used in combination with different other azo compounds.

Figure 2:
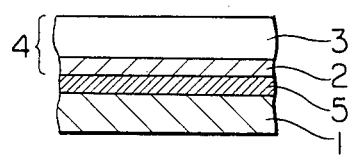
Figure 3:
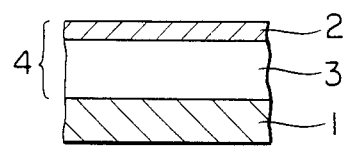
Figure 4:
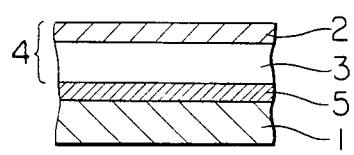
Figure 5:
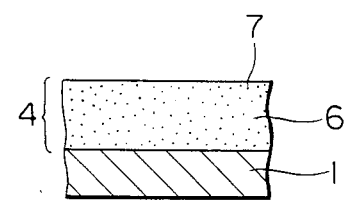
Figure 6:
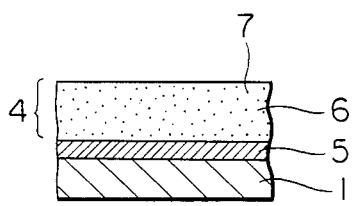

Regarding the mechanical construction of electrophotographic photoreceptors, various forms are known. The electrophotographic photoreceptor of this invention is allowed to take any of the forms. It takes usually the forms shown in FIGS. 1 to 6. In FIGS. 1 and 3, conductive support 1 has thereon a photosensitive layer 4 composed of a carrier-generating layer 2 consisting principally of the foregoing azo compound and a carrier-transport layer 3 consisting principally of a carrier-transport material. As shown in FIGS. 2 and 4, the photosensitive layer 4 is allowed to be provided through an interlayer 5 on the conductive support. Thus, when photoconductive layer 4 is provided in the two-layer construction, an electrophotographic photoreceptor having the most excellent electrophotographic characteristics can be obtained. And in the present invention, as shown in FIGS. 5 and 6, photosensitive layer 4 comprised of the foregoing carrier-generating material 7 dispersed into a layer 6 consisting principally of a carrier-transport material is allowed to be provided directly or through an interlayer 5 on conductive support 1.

In the case where the azo compound of the present invention is used as the carrier-generating material, the carrier-transport material usable in combination with this includes electron-accepting materials liable to transport electrons, such as trinitrofluorenone or tetranitrofluorenone; polymers having as the side chain thereof heterocyclic compounds typified by poly-N-vinylcarbazole; and electron-donating materials liable to transport positive holes, such as triazole derivatives, oxadiazole derivatives, imidazole derivatives, pyrazoline derivatives, polyarylalkane derivatives, phenylenediamine derivatives, hydrazone derivatives, amino-substituted chalcone derivatives, triarylamine derivatives, carbazole derivatives, stilbene derivatives, and the like. The carrier-transport materials usable in the present invention, however, are not limited to the above materials.

The carrier-generating layer 2, which is an integral part of the two-layer-construction photosensitive layer 4, may be formed on conductive support 1 or directly on or, if necessary, through an interlayer such as an adherent layer or barrier layer on carrier-transport layer 3, for example, in the following manners:

(M-1) A solution prepared by dissolving the azo compound into an appropriate solvent or a solution, prepared by, if necessary, additionally mixing and dissolving a binder material into the above solution is coated.

(M-2) The azo compound is, dispersed in the fine particulate form into a dispersion medium by means of a ball mill, homomixer, or the like, and, if necessary, a binder material is additionally mixed and dispersed thereinto, thereby preparing a dispersed liquid, which is then coated.

The solvent or dispersion medium for use in forming the carrier-generating layer includes n-butylamine, diethylamine, ethylenediamine, isopropanolamine, triethanolamine, triethylenediamine, N,N-dimethylformamide, acetone, methyl-ethyl ketone, cyclohexanone, benzene, toluene, xylene, chloroform, 1,2-dichloroethane, dichloromethane, tetrahydrofuran, dioxane, methanol, ethanol, isopropanol, ethyl acetate, butyl acetate, dimethylsulfoxide, and the like.

Where a binder material is used in the carrier-generating layer or carrier-transport layer, the binder material may be any arbitrary one, but desirable to be a hydrophobic, highly dielectric, electrically insulating film-formable high-molecular polymer. Such the high-molecular polymer includes, for example, the following compounds, but is not limited thereto.

(P-1) Polycarbonate
(P-2) Polyester
(P-3) Methacryl resin
(P-4) Acryl resin
(P-5) Polyvinyl chloride
(P-6) Polyvinylidene chloride
(P-7) Polystyrene
(P-8) Polyvinyl acetate
(P-9) Styrene-butadiene copolymer
(P-10) Vinylidene chloride-acrylnitrile copolymer
(P-11) Vinyl chloride-vinyl acetate copolymer
(P-12) Vinyl chloride-vinyl acetate-maleic anhydride copolymer
(P-13) Silicone resin
(P-14) Silicone-alkyd resine
(P-15) Phenol-formaldehyde resin
(P-16) Styrene-alkyd resin
(P-17) Poly-N-vinylcarbazole
(P-18) Polyvinylbutyral These binder materials may be used alone or in a mixture of two or more thereof.

The thickness of the thus formed carrier-generating layer 2 is preferably from 0.01 μm to 20 μm, and more preferably from 0.05 μm to 5 μm. The thickness of the carrier-transport layer is preferably from 5 μm to 30 μm. If the carrier-generating layer or photosensitive layer is of the dispersion system, the dispersed particle size of the azo compound is preferably not more than 5 μm, and more preferably not mote than 1 μm.

Materials usable as the conductive support of the electrophotographic photoreceptor of the invention include plates and drums made of metals including alloys; conductive compounds such as conductive polymers, indium oxide, etc.; paper, plastic film, etc., rendered conductive by being coated, vacuum-deposited, or laminated thereon with a thin layer of a metal such as aluminum, palladium, gold, or an alloy thereof; and the like. Materials usable as the interlayer such as an adherent layer or barrier layer include organic high-molecular materials such as polyvinyl alcohol, ethyl cellulose, carboxymethyl cellulose, etc., and aluminum oxide, in addition to the previously mentioned high-molecular polymers used as the binder.

The electrophotographic photoreceptor of this invention is of such the construction as has been described above, and, as will be apparent from the examples described hereinafter, excellent in the charging, sensitivity and image-forming characteristics as well as in the durability; that is, the photoreceptor is little deteriorated even when used repeatedly.

SYNTHESIS EXAMPLES

The azo compounds of this invention may be synthesized by combined generally known methods. Synthesis examples will be given below:

SYNTHESIS EXAMPLE 1

Synthesis of Exemplified Compound A-(4)

(1) Synthesis of intermediate phenoxazine:

The synthesis was performed in accordance with the method disclosed by Paulette Müller et al. (J. Org. Chem. Vol. 24, 37 (1959)).

Two hundred eighteen grams of o-aminophenol and 1 g of iodine were put in a flask, and fused by heating to 270°–290° C. for three hours. On the other hand, 80 g of sodium hydroxide were dissolved into 4 liters of water. The above fused reaction product was poured little by little into this aqueous solution. The deposited crystals were filtered and washed with water, and then thermally extracted (at 70°–60° C.) from toluene. The extract solution was filtered through 100 g of silica gel (300 mesh), and the filtrate was concentrated under reduced pressure. To this were then added 100 ml of methanol. The resulting crystals were filtered, and then washed with a small amount of methanol, whereby an objective product was obtained (yield: 25.0 g, 13.7%, M.P.: 152° to 154° C.).

(2) Synthesis of acetylphenoxazine:

Twenty-three point eight grams (0.13 mole) of the phenoxazine were dispersed into 50 ml of glacial acetic acid, and to this were added 80 ml of acetic anhydride. This mixture was refluxed by heating for two hours. After completion of the reaction, the solvent was evaporated to dry the product under reduced pressure. The resulting residuum was refined by being suspendedly washed in 50 ml of methanol (yield: 25.2 g; 80%, M.P.: 143° to 144° C.).

(3) Synthesis of intermediate 2,7-dinitroacetylphenoxazine:

The synthesis was performed in accordance with the method disclosed by F. Kehrmann et al. (Ber. Vol. 36, 475 (1903)).

Twenty-four point eight grams (0.11 mole) of the acetylphenoxazine were dissolved into 300 ml of glacial acetic acid. To this solution were added dropwise 30 ml of concentrated nitric acid (d=1.42) at 25° C., and the mixture was stirred for three hours at the same temperature. After that, 30 ml of acetic anhydride were added to this, and the liquid was stirred for another hour. After the reaction, to this were added 200 ml of water, and the resulting crystals were filtered, washed with water and then with methanol, whereby an objective product was obtained (yield: 22.5 g; 70%, M.P.: 185° to 190° C.).

(4) Synthesis of intermediate 2,7-dinitrophenoxazine:

Twenty-two point five grams of the 2,7-dinitroacetylphenoxazine were dispersed into a mixture of 250 ml of ethanol with 50 ml of concentrated hydrochloric acid, and the dispersed liquid was refluxed by heating for five hours. After the reaction, another 50 ml of concentrated hydrochloric acid were added to this, and the crystals that were deposited after cooling were filtered, whereby 15.5 g of an objective product in red color were obtained (yield: 84.4%, M.P.: not less than 260° C. (blackened)).

(5) Synthesis of intermediate 10-ethyl-2,7-dinitrophenoxazine:

Seven point eight grams of the 2,7-dinitrophenoxazine were dispersed into 100 ml of acetone, and to this were added 15 g of potassium carbonate and 9 g of diethyl sulfate, and the liquid was refluxed by heating for 10 hours. After the reaction, to the reaction liquid were added 200 ml of water, and the deposited crystals were filtered and then washed with water. The crude crystal product was vigorously stirred in a mixture of 200 ml of methanol, 3 g of sodium hydroxide and 300 ml of water to remove the unreacted material, whereby an objective intermediate 10-ethyl-2,7-dinitrophenoxazine (yield: 8.0 g; 88.0%, M.P.: 253° to 256° C.).

(6) Synthesis of intermediate 10-ethyl-2,7-diaminophenoxazine:

Seven point five grams of the 10-ethyl-2,7-dinitrophenoxazine and 15 g of iron powder were dispersed into a mixture of 70 ml of N,N-dimethylformamide with 15 ml of water, and to the mixture were added 2 ml of concentrated hydrochloric acid to effect its reaction for an hour at about 105° C. Upon completion of the reaction, the liquid was neutralized by adding 3 g of sodium carbonate and 5 ml of water thereto, and then filtered while it is hot. The residuum was washed with a small quantity of heated N,N-dimethylformamide, and then the filtrate was poured into 1 liter of cool water containing 2 g of sodium hydroxide. The produced crystals were filtered, washed with water, and then dried in brown desiccator (yield: 4.7 g; 79%).

(7) Synthesis of Exemplified Compound A-(4):

Two point five grams of the 10-ethyl-2,7-diaminophenoxazine were dissolved into 30 ml of concentrated sulfuric acid, and to this solution was added dropwise a beforehand prepared nitrosylsulfuric acid (10 ml of concentrated sulfuric acid and 1.6 g of sodium nitrite) at 0° C. After completion of the dropping, the liquid was stirred for 30 minutes at the same temperature, and then poured into one liter of iced water containing 10 g of ammonium hexafluorophosphate. The deposited crystals (tetrazonium hexafluorophosphate) was filtered, washed with a small amount of cool water, and then dissolved into 100 ml of N,N-dimethylformamide. This solution was used as the dropping liquid to the following coupling reaction.

On the other hand, 7.8 g of hydroxy-3-(2-methyl-4-methoxyphenylcarbamoyl)benzo[a]carbazole (Naphthol ASSR, a product of Hoecht) and 10 g of triethanolamine were dissolved into 300 ml of N,N-dimethylformamide. To this solution, being cooled by ice to 0°–5° C., was added dropwise the above tetrazonium salt solution. The reaction liquid, after being stirred for two hours at the same temperature, was allowed to stand overnight at room temperature. The deposited crystals were filtered, washed twice with 300 ml of N,N-dimethylformamide and once with one liter of acetone, and then dried, whereby 3.8 g of Exemplified Compound A-(4) were obtained (yield: 36.0%).

This compound was ascertained by elementary analysis.

| (Chemical formula: $C_{64}H_{49}N_9O_7$) | | | |
|---|---|---|---|
| Element | C | H | N |
| Found (%) | 72.61 | 4.82 | 11.90 |
| Calculated (%) | 72.77 | 4.68 | 11.94 |

SYNTHESIS EXAMPLE 2

Synthesis of Exemplified Compound A-(10)

Five point eight grams of 2-hydroxy-3-(2,4-dimethylphenylcarbamoyl)naphthalene and 10 ml of triethanolamine were dissolved into 350 ml of N,N-dimethylformamide, and to this solution, being cooled by ice to 0°-5° C., were added dropwise the foregoing tetraazonium salt solution prepared in the same manner as in Synthesis Example-1. The liquid was stirred for two hours at the same temperature, and then allowed to stand overnight at room temperature. The thus formed crystals were filtered. The crystalline product was washed twice with 500 ml of N,N-dimethylformamide and then once with one liter of acetone, and then dried, whereby 4.5 g of Compound A-(10) were obtained (yield: 54.8%).

This compound was ascertained by elementary analysis.

| (Chemical formula: $O_{50}H_{43}N_7O_5$) | | | |
|---|---|---|---|
| Element | C | H | N |
| Found (%) | 72.93 | 5.41 | 9.80 |
| Calculated (%) | 73.07 | 5.27 | 9.73 |

SYNTHESIS EXAMPLE 3

Synthesis of Exemplified Compound A-(43)

(1) Synthesis of intermediate dinitrophenothiazine:

The synthesis was performed in accordance with the method disclosed by C. Bodea and M. Raileau (Chem. Abst. Vol. 54, 22657g (1960)).

Twenty-five grams of phenothiazine were dissolved into a mixture solution of 600 ml of chloroform with 50 ml of glacial acetic acid, and to this were little by little added 25 g of sodium nitrite, spending about an hour. After the addition, the liquid was stirred for two hours, and the produced crystals were filtered, washed well with methanol and then with water. The product was recrystallized from MDF (N,N-dimethylformamide), whereby 14 g of an intermediate dinitrophenothiazine were obtained (yield: 38.6%).

(2) Synthesis of intermediate N-P-tolyldinitrophenothiazine:

Eight point seven grams of the dinitrophenothiazine and 10 g of p-iodotoluene were mixed into 50 ml of nitrobenzene, and to this mixture were added 8 g of potassium carbonate and 0.5 g of copper powder, and the reaction of them took place at 210°-220° C. over a period of 10 hours. After completion of the reaction, the nitrobenzene and the residual p-iodotoluene were distilled off by steam distillation, and the produced crude crystals were filtered. One point five liters of chloroform were added to the crude crystals thereby to be thermally extracted therefrom. The extract solution was filtered through 50 g of silica gel (200 mesh), and the filtrate was evaporated to be dried. The residuum was suspendedly washed in a small amount of ethyl acetate, and then washed well with a mixture liquid of 50 ml of methanol, 3 g of sodium hydroxide, and 5 ml of water. This was further washed with water and then with methanol, whereby 5.1 g of an objective intermediate in red color N-P-tolyldinitrophenothiazine were obtained (yield: 45%, M.P.: 185° to 188° C.).

(3) Synthesis of intermediate 2,7-diamino-10-tolyl-phenothiazine and Exemplified Compound A-(43):

Three point eight grams of the N-P-tolyldinitrophenothiazine were suspended in 150 ml of concentrated hydrochloric acid, and to this were added 40 g of stannous chloride (dihydrated). The liquid was refluxed by heating for three hours. The crystals formed after cooling were filtered and then washed with dilute hydrochloric acid, whereby 2,7-diamino-10-tolylphenothiazine-tin complex was obtained (M.P.: 195° to 200° C.).

The above diamino-tin complex was all dispersed into a solution of 20 ml of hydrochloric acid dissolved in 150 ml of water. To this dispersed liquid was added dropwise at −5° C. a solution of 1.5 g of sodium nitrite dissolved in 10 ml of water. After the dropping, the reaction liquid was stirred at the same temperature for 30 minutes and, immediately after that, was filtered. To the resulting filtrate were added 10 g of ammonium hexafluorophosphate, and the formed crystals were filtered, whereby tetraazonium hexafluorophosphate was obtained. The crystals were dissolved into 100 ml of N,N-dimethylformamide, and this solution was used as a dropping liquid to the following coupling reaction.

Subsequently, 7.0 g of 2-hydroxy-3-(4-methoxy-phenylcarbamoyl)benzo[a]carbazole (Naphthol AS-SG, a product of Hoecht) and 10 g of triethanolamine were dissolved into 300 ml of N,N-dimethylformamide, and to this solution, being cooled by ice to 5° C., was added dropwise the above tetraazonium salt solution. The reaction liquid, after being stirred at the same temperature for two hours, were allowed to stand overnight at room temperature, and the thus formed crystals wee then filtered. The filtered crystals were washed twice with 300 ml of N,N-dimethylformamide and then twice with one liter of acetone, and then dried, whereby 4.8 g of Exemplified Compound A-(43) was obtained (yield: 43% (from the dinitro compound)).

This compound was ascertained by elementary analysis.

| (Chemical formula: $C_{67}H_{47}N_9O_6S$) | | | | |
|---|---|---|---|---|
| Element | C | H | N | S |
| Found (%) | 72.49 | 4.36 | 11.35 | 3.15 |
| Calculated (%) | 72.74 | 4.28 | 11.40 | 2.90 |

SYNTHESIS EXAMPLE 4

Synthesis of Exemplified Compound A-(100)

(1) Synthesis of intermediate phenoxazine:

The synthesis was carried out in accordance with the method disclosed by Paulette Müller et al. (J. Org. Chem. Vol. 24, 37 (1959)).

Two hundred eighteen grams of o-aminophenol and 1 g of iodine were put in a flask, and fused by heating to 270°–290° C. for three hours. On the other hand, 80 g of sodium hydroxide were dissolved into 4 liters of water. The above fused reaction product was poured little by little into this aqueous solution. The deposited crystals were filtered and washed with water, and then thermally extracted (at 70°–60° C.) from toluene. The extract solution was filtered through 100 g of silica gel (300 mesh), and the filtrate was concentrated under reduced presure. To this were then added 100 ml of methanol. The resulting crystals were filtered, and then washed with a small amount of methanol, whereby an objective product was obtained. Yield: 25.0 g; 13.7%, M.P.: 152° to 154° C.

(2) Synthesis of acetylphenoxazine:

Twenty-three point eight grams (0.13 mole) of the phenoxazine were dispersed into 50 ml of glacial acetic acid, and to this were added 80 ml of acetic anhydride. This mixture was refluxed by heating for two hours. After completion of the reaction, the solvent was evaporated to dry the product under reduced pressure. The resulting residuum was refined by being suspendedly washed in 50 ml of methanol.

Yield: 25.2 g; 86%, M.P.: 143° to 144° C.

(3) Synthesis of intermediate 2,7-dinitroacetylphenoxazine:

The synthesis was performed in accordance with the method disclosed by F. Kehrmann et al. (Ber. Vol. 36, 475 (1903)).

Twenty-four point eight grams (0.11 mole) of the acetylphenoxazine were dissolved into 300 ml of glacial acetic acid. To this solution were added dropwise 30 ml of concentrated nitric acid (d=1.42) at 25° C., and the mixture was stirred for three hours at the same temperature. After that, 30 ml of acetic anhydride were added to this, and the liquid was stirred for another hour. After the reaction, to this were added 200 ml of water, and the resulting crystals were filtered, washed with water and then with methanol, whereby an objective product was obtained. Yield: 22.5 g; 70%, M.P.: 185° to 190° C.

(4) Synthesis of intermediate 2,7-dinitrophenoxazine:

Twenty-two point five grams of the 2,7-dinitroacetylphenoxazine were dispersed into a mixture of 250 ml of ethanol with 50 ml of concentrated hydrochloric acid, and the dispersed liquid was refluxed by heating for five hours. After the reaction, another 50 ml of concentrated hydrochloric acid were added to this, and the crystals that were deposited after cooling were filtered, whereby 15.5 g of an objective product in red color were obtained. Yield: 84.4%, M.P.: not less than 260° C. (blackened).

(5) Synthesis of intermediate 2,7-dinitro-10-p-nitrophenylphenoxazine:

Eight point five grams of the dinitrophenoxazine and 12.0 g of p-nitroiodobenzene were mixed with 50 ml of nitrobenzene. To this mixture were added 10.g of potassium carbonate and 0.5 g of powdery copper, and the reaction of them took place at 200°–210° C. for 15 hours. After the reaction, the nitrobenzene was distilled off by steam distillation to thereby deposit crude crystals, which was then filtered. The crystals were thermally extracted in three liters of chloroform. The extract solution was filtered through 50 g of silica gel (200 mesh), and the filtrate was concentrated. The concentrated filtrate was crystallized by use of a small amount of ethyl acetate; washed by being suspended in ethyl acetate; and then sufficiently stirred to be suspended in a mixture of 50 ml of methanol, 50 ml of acetone, 3 g of sodium hydroxide and 15 ml of water to thereby remove the unreacted components. Further, the product was washed with water and then with methanol, whereby 3.9 g of an objective intermediate 2,7-dinitro-10-p-nitrophenylphenoxazine were obtained. Yield: 31.6%, M.P.: 285° to 290° C.

(6) Synthesis of intermediate 2,7-diamino-10-p-aminophenylphenoxazine and of Exemplified Compound A-(100):

Two grams of the 2,7-dinitro-10-p-nitrophenylphenoxazine were dispersed into 100 ml of concentrated hydrochloric acid, and to this were added 25 g of stannous chloride (dihydrated), and the mixture was refluxed by heating for three hours. After cooling, the deposited crystals were filtered and then washed with 5 ml of dilute hydrochloric acid to thereby obtain a 2,7-diamino-10-p-aminophenylphenoxazine-tin complex.

The whole amount of the above triamino-tin complex was dissolved into 20 ml of concentrated sulfuric acid. To this solution were added dropwise an in-advance prepared nitrosylsulfuric acid (8 ml of concentrated sulfuric acid and 1.4 g of sodium nitrate) at a temperature of from 0° to 5° C. After the dropping, the mixture was stirred at the same temperature for an hour, and then poured into 500 ml of an iced water containing 10 g of ammonium hexafluorophosphate. The produced crystals were filtered to obtain hexazonium hexafluorophosphate. The crystals were dissolved into 100 ml of N,N-dimethylformamide. This solution was used as a dropping liquid to the subsequent coupling reaction.

Subsequently, 5.8 g of 2-hydroxy-3-(2-methyl-4-methoxyphenylcarbamoyl)-benzo[a]carbazole (Naphthol ASSR, a product of Hoecht) and 10 ml of triethanolamine were dissolved into 250 ml of N,N-dimethylformamide, and to this solution, being cooled by ice to 0°–5° C., was added dropwise the above hexaazonium salt solution. Further, the liquid, after being stirred for two hours at the same temperature, was allowed to stand overnight at room temperature, and the thus produced crystals were then filtered. The crystalline product was washed twice with 200 ml of N,N-dimethylformamide and then another twice with one liter of acetone, and then dried, whereby 1.3 g of Compound A-(100) were obtained. Yield: 17% (from the trinitro compound)

This compouned was ascertained by elemental analysis.

| (Chemical formula: $C_{93}H_{57}N_{13}O_{10}$) | | | |
|---|---|---|---|
| Element | C | H | N |
| Found (%) | 72.98 | 4.52 | 12.01 |
| Calculated (%) | 73.17 | 4.42 | 11.93 |

EXAMPLES

The following examples will further illustrate the present invention, but the embodiment of the invention is not limited thereto.

Example-1

Two grams of Exemplified Compound A-(44) and 2 g of polycarbonate resin "Panlite L-1250" (a product of Teijin Chemical Industry Co., Ltd.) were added to 110 ml of 1,2-dichloroethane, and dispersed by means of a ball mill over a period of 12 hours. The dispersed liquid was coated on an aluminum-vacuum-deposited polyester film support so that its dry thickness is 1 μm, thus forming a carrier-generating layer. Further, on this was coated a liquid prepared by dissolving 6 g of the following compound K-1 and 10 g of polycarbonate resin "Panlite L-1250" into 110 ml of 1,2-dichloroethane to form a carrier-transport layer having a dry thickness of 15 μm, whereby an electrophotographic photoreceptor of the invention was prepared.

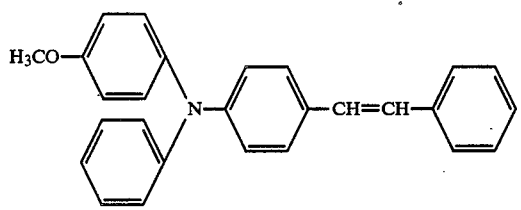

K-1

The thus obtained photoreceptor was evaluated with respect to the following characteristics by use of an Electrostatic Paper Tester SP-428 (manufactured by Kawaguchi Denki Seisakusho K. K.). The photoreceptor was electrostatically charged for 5 seconds in the dark, and then exposed to a halogen lamp light so that the illuminance on the surface of the photoreceptor is 35 lux, and then the exposure (half-value exposure) E ½, required to attenuate by half the surface electric potential, was found. And the surface electric potential (residual potential) $V_R$ of the photoreceptor after being exposed at an exposure of 30 lux.sec. also was found. Further, the same experiments and measurements were repeated 100 times. The results are as given in Table 1.

TABLE 1

|  | 1st | 100th |
|---|---|---|
| E ½(lux. sec) | 2.0 | 2.0 |
| $V_R$(V) | 0 | 0 |

Example-2

A sample was prepared in the same manner as in Example-1, except that the Exemplified Compound A-(44) used in Example-1 was replaced by the same amount of Exemplified Compound A-(106) and was then evaluated in the same manner as in Example-1. The results thereof are given in Table 2.

TABLE 2

|  | 1st | 100th |
|---|---|---|
| E ½(lux. sec) | 2.3 | 2.3 |
| $V_R$(V) | 0 | 0 |

Comparative Example-1

A comparative photoreceptor sample was prepared in the same manner as in Example-1 except that the following azo compound (G-1) was used as the carrier-generating material.

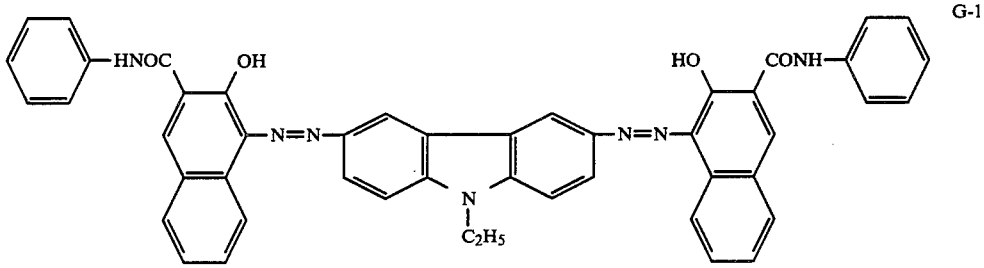

G-1

This comparative electrophotographic photoreceptor was tested and measured in the same manner as in Example-1. The obtained results are given in Table 3.

TABLE 3

|  | 1st | 100th |
|---|---|---|
| E ½(lux. sec) | 3.2 | 4.1 |
| $V_R$(V) | −20 | −90 |

As is apparent from the above results, the electrophotographic photoreceptor of the invention is very excellent in the speed, residual electric potential and stability when used repeatedly as compared to the comparative electrophotographic photoreceptor.

Example-3

On an aluminum foil-laminated polyester film support was provided a 0.05 μm-thick interlayer comprised of a vinyl chloride-vinyl acetate-maleic anhydride copolymer "Eslec MF-10" (a product of Sekisui Chemical Co., Ltd.), on which was then further coated a dispersion liquid prepared by mixing 2 g of Exemplified Compound A-(50) into 110 ml of 1,2-dichloroethane and dispersing it over a period of 24 hours by means of a ball mill to form a carrier-generating layer with a dry thickness of 0.5 μm. On this carrier-generating layer a liquid prepared by dissolving 6 g of 4-methoxytriphenylamine and 10 g of methacryl resin "Acrypet" (a product of Mitsubishi Rayon Co., Ltd.) into 70 ml of 1,2-dichloroethane was coated so that its dry thickness is 10 μm to thereby form a carrier-transport layer, whereby an electrophotographic photoreceptor was produced.

This electrophotographic photoreceptor was tested and meausred in the same manner as in Example-1. The results obtained in the first measurement were: E ½=2.5 lux.sec. and $V_R$=OV.

Example-4

An electrophotographic photoreceptor was prepared in the same manner as in Example-3, except that the Exemplified Compound A-(50) used in Example-3 was replaced by the same amount of Exemplified Compound A-(107) and was then measured in the same manner as taken in Example-1. The results obtained were: E ½=2.0 lux.sec., and $V_R$=OV.

Example-5

An ethylenediamine 1% Exemplified Compound A-(68) solution was coated so that its dry thickness is 0.3 μm on an interlayer (used in Example-3)-provided conductive support, whereby a carrier-generating layer was formed. On this was coated a liquid prepared by dissolving 6 g of the following compound K-2 and 10 g of a polyester resin "Vylon 200" (a product of Toyo Spinning Co., Ltd.) into 70 ml of 1,2-dichloroethane to form a carrier-transport layer so that its dry thickness is 12 μm, whereby an electrophotographic photoreceptor of the present invention was produced.

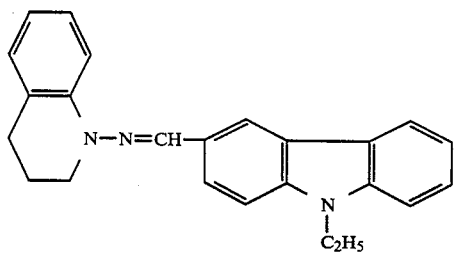

K-2

This electrophotographic photoreceptor was tested and measured in the same manner as in Example-1, and then the results as shown in Table 4 were obtained.

TABLE 4

|  | 1st | 100th |
|---|---|---|
| E ½(lux. sec) | 1.9 | 1.9 |
| $V_R$(V) | 0 | 0 |

Example-6

An electrophotographic photoreceptor was prepared in the same manner as in Example-5, except that the Exemplified Compound used in Example-5 was replaced by the same amount of Exemplified Compound A-(127), and was then measured in the same manner as in Example-1. The results thereof are given in Table-5.

TABLE 5

|  | 1st | | 100th | |
|---|---|---|---|---|
|  | E ½(lux. sec) | $V_R$(V) | E ½(lux. sec) | $V_R$(V) |
| Example-3 | 2.5 | 0 | 2.5 | 0 |

Example-7

A carrier-generating layer was formed in the same manner as in Example-5 except that the Exemplified Compound A-(68) was replaced by Exemplified Compound A-(9). On this was coated a liquid prepared by dissolving 6 g of the following compound K-3 and 10 g of a polycarbonate "Panlite L-1250" (a product of Teijin Chemical Industry Co., Ltd.) into 70 ml of 1,2-dichloroethane to form a carrier-transport layer so that its dry thickness is 10 μm, whereby an electrophotographic photoreceptor of the present invention was prepared.

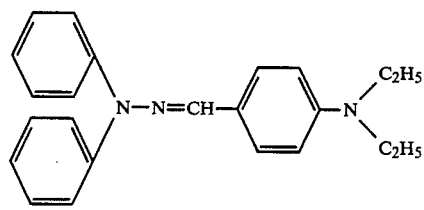

K-3

This electrophotographic photoreceptor was tested and meaured in the same manner as in Example-1. The obtained results were: E ½=3.1 lux.sec. and $V_R$=OV.

Example-8

An electrophotographic photoreceptor was prepared in the same manner as in Example-5, except that the Exemplified Compound A-(68) used in Example-5 was replaced by Exemplified Compound A-(107), and was then measured in the same manner as in Example-1. The results thereof were: E ½=2.7 lux.sec., and $V_R$=OV.

Example-9

On the surface of a 100 mm-diameter aluminum drum was provided a 0.05 μm-chick interlayer consisting of a vinyl chloridevinyl acetate-maleic anhydride copolymer "Eslec MF-10" (a product of Sekisui Chemical Co., Ltd.). On this was coated a dispersion liquid prepared by mixing 4 g of Exemplified Compound A-(43) into 400 ml of 1,2-dichloroethane and dispersing it over a period of 24 hours by means of a ball mill disperser to form a carrier-generating layer so that its dry thickness is 0.6 μm. On this was further coated a liquid prepared by dissolving 30 g of the following compound K-4 and 50 g of a polycarbonate resin "Iupilon S-1000" (a product of Mitsubishi Gas Chemical Co., Ltd.) into 400 ml of 1,2-dichloroethane to thereby form a carrier-transport layer so that its dry thickness is 13 μm, whereby a drum-type electrophotographic photoreceptor of the present invention was produced.

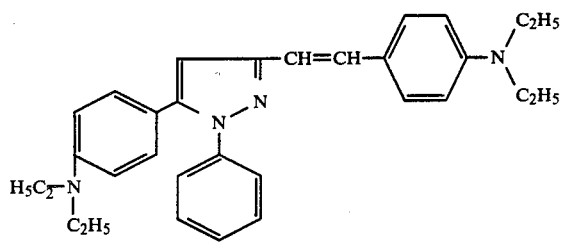

K-4

The thus prepared photoreceptor was loaded in a remodeled unit of Electrophotographic Copier "U-Bix V₂" (manufactured by Konishiroku Photo Industry Co., Ltd.) to make copies of an image, whereby high-contrast, truly reproduced, clear image copies were obtained. The quality of the image was consistent even when the copying operation was repeated 10,000 times.

Example-10

An electrophotographic photoreceptor was prepared in the same manner as in Example-9, except that the Exemplified Compound A-(43) used in Example-9 was replaced by the same amount of Exemplified Compound A-(100), and was then put to the same copying tests. Resultantly, high-contrast, truly-reproduced, clear-image copies were obtained similarly to those obtained in the case of Example-9. The quality of every image copy was consistent even when copying 10,000 times repeatedly.

Comparative Example-2

A drum-type comparative photoreceptor was prepared in the same manner as in Example-9 except that the Exemplified Compound A-(43) used in Example-5 was replaced by the following formula-having azo compound G-2, and the prepared photoreceptor was used to produce copies. When the copies were evaluated in the same manner as in Example-9, they were found out to be of foggy image. As the copying operation was continued repeatedly, the contrast of the copy image became lowered. After producing 2,000 copies, almost no image reproduction was obtained.

mer "Eslec MF-10" (a product of Sekisui Chemical Co., Ltd.), and on this was then coated a dispersion liquid prepared by mixing 4 g of Exemplified Compound A-(43) into 400 ml of 1,2-dichloroethane and dispersing it over a period of 24 hours by means of a ball mill disperser to thereby form a carrier-generating layer so that its dry thickness is 0.5 μm. On this was further coated a liquid prepared by dissolving 30 g of 4-methyl-4'-styryl-triphenylamine and 50 g of a polycarbonate resin "Pan-lite L-1250" (a product of Teijin Chemical Industry Co., Ltd.) into 400 ml of 1,2-dichloroethane to form a carrier-transport layer so that its dry thickness is 12 μm, where by a drum-type electrophotographic photoreceptor of the present invention was produced.

The spectral sensitivity of this photoreceptor at 780 nm was 1.09 uJ/cm² (half-value exposure).

This photoreceptor was subsequently used to make practical exposure tests with a testing machine equipped with a semiconductor laser (780 nm) unit, emitting a laser light whose intensity at the surface of the photoreceptor is 0.85 mW.

The surface of the photoreceptor, after being charged at −6 KV, was exposed to the laser light and subjected to reversal development by the application of a bias voltage, and then a satisfactory image with no fog was obtained. The image quality was consistent even after the test was repeated 10,000 times.

Example-12–16

A drum-type electrophotographic photoreceptor was prepared in the same manner as in Example-11 except that the Exemplified Compound A-(43) in Example-6 was replaced by Exemplified Compound A-(1). The spectral sensitivity of this photoreceptor at 780 nm was 1.30 uJ/cm² (half-value exposure).

Five drum-type electrophotographic photoreceptors were prepared in the same manner as in Example-11 except that the Exemplified Compound A-(43) in Example-11 was replaced by Exemplified Compounds A-(42) A-(102), A-(103), A-(104) and A-(105). The spectral sensitivities of the respective photoreceptors at 780 nm are as given in Table 6.

TABLE 6

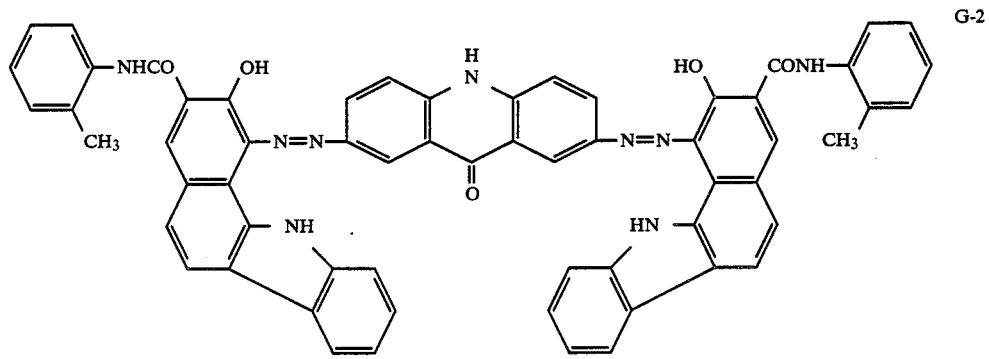

G-2

Example-11

On the surface of a 100 mm-diameter aluminum drum was provided a 0.05 μm-thick interlayer consisting of a vinyl chloridevinyl acetate-maleic anhydride copoly-

| Example No. | 12 | 13 | 14 | 15 | 16 |
|---|---|---|---|---|---|
| Carrier-generating material (Exemplified Com- | A-(42) | A-(102) | A-(103) | A-(104) | A-(105) |

TABLE 6-continued

| Example No. | 12 | 13 | 14 | 15 | 16 |
|---|---|---|---|---|---|
| pound) | | | | | |
| Half-value exp. (uJ/cm²) | 1.30 | 1.00 | 0.89 | 0.90 | 0.95 |

These photoreceptors each produced a satisfactory image free of fog in the practical exposure test with the same testing machine as was used in Example-11, and the image quality obtained was consistent even after the test was repeated 10000 times.

What is claimed is:

1. A photoreceptor comprising a photosensitive layer and an electroconductive support, wherein said photosensitive layer contains an azo compound represented by the following Formula [I];

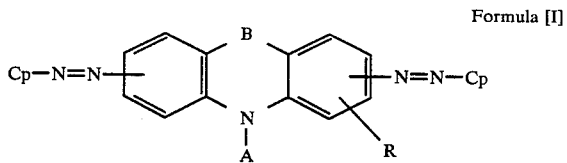

Formula [I]

wherein A is a substituted or unsubstituted alkyl group, or a substituted or unsubstituted arlyl group, B is oxygen atom or sulfur atom; R is hydrogen atom, an alkyl group, an alkoxy group, or a halogen atom; and Cp is

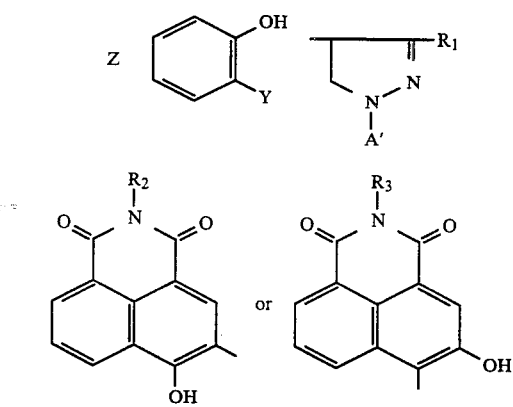

wherein
Z represents a group of atoms necessary for constituting a substituted or unsubstituted aromatic carbon ring, or a substituted or unsubstituted aromatic heterocyclic ring;
Y is a substituted or unsubstituted carbamoyl group or a substituted or unsubstituted sulfamoyl group;
$R_1$ is hydrogen atom, a substituted or unsubstituted amino group, a substituted or unsubstituted carbamoyl group, a carboxy group and the esters thereof, or cyano group;
A' is a substituted or unsubstituted aryl group;
$R_2$ and $R_3$ are a substituted or unsubstituted alkyl group, or a substituted or unsubstituted aralkyl group, or a substituted or unsubstituted aryl group, respectively.

2. The photoreceptor of claim 1, wherein said B is oxygen atom.

3. The photoreceptor of claim 1, wherein said B is sulfur atom.

4. The photoreceptor of claim 2 or 3, wherein said A is a group represented by the following formula;

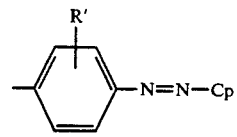

wherein R' is hydrogen atom, an alkyl group, an alkoxy group, or a halogen atom.

5. The photoreceptor of claim 2, wherein said compound is represented by the following Formula [II];

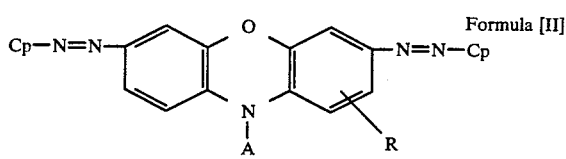

Formula [II]

6. The photoreceptor of claim 3, wherein said compound is represented by the following Formula [III];

Cp—N=N—⟨⟩—S—⟨⟩—N=N—Cp

Formula [III]

7. The photoreceptor of claim 2, wherein said compound is represented by the following Formula [IV];

Formula [IV]

Cp—N=N—⟨⟩—O—⟨⟩—N=N—Cp

8. The photoreceptor of claim 3, wherein said compound is represented by the following Formula [V];

Formula [V]

Cp-N=N—⟨⟩—S—⟨⟩—N=N—Cp

9. The photoreceptor of claim 5, wherein said compound is represented by the following Formula [VI];

Formula [VI]

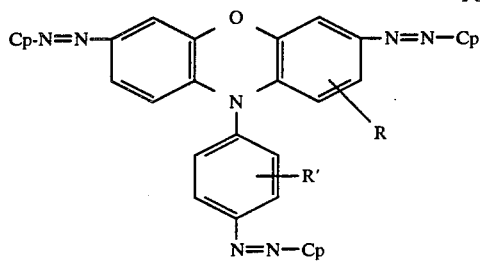

10. The photoreceptor of claim 6, wherein said compound is represented by the following Formula [VII];

Formula [VII]

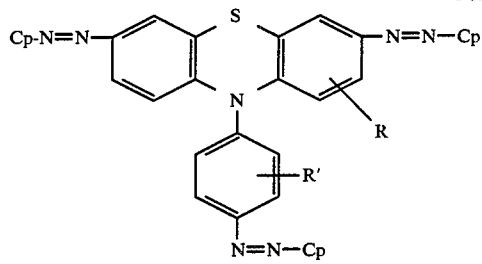

11. The photoreceptor of claim 7, wherein said compound is represented by the following Formula [VIII];

Formula [VIII]

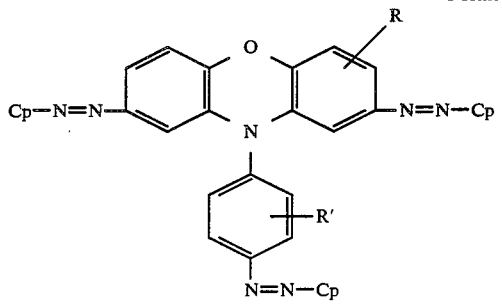

12. The photoreceptor of claim 8, wherein said compound is represented by the following Formula [IX];

Formula [IX]

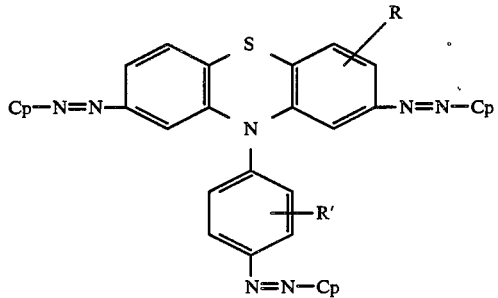

13. The photoreceptor of claim 5, 6, 7, or 8, R is a hydrogen atom.

14. The photoreceptor of claim 9, 10, 11, or 12, R and R' is a hydrogen atom.

15. The photoreceptor of claim 1, wherein said photosensitive layer consists of a carrier generation layer which contains said azo compound as a carrier generating substance and a carrier transport layer which contains a carrier transporting substance.

16. The photoreceptor of claim 15, wherein said carrier transporting substance is selected from the group consisting of trinitrofluorenone, tetronitrofluorenone, poly-N-vinylcarbazole, a triazole derivative, oxadiazole derivative, imidazol derivative, a pyrazolone derivative, polyaryl alkane derivative, phenylene diamine derivative, hydrazone derivative, amine substituted alkene derivative, triaryl amine derivative, carbazole derivative, and stylbene derivative.

17. The photoreceptor of claim 15, wherein said carrier generation layer has the thickness in the range of from 0.01 μm to 20 μm.

18. The photoreceptor of claim 15, wherein said carrier transport layer has the thickness in the range of from 5 μm to 30 μm.

19. The photoreceptor of claim 1, wherein said photosensitive layer is a single layer which contains said azo compound as a carrier generating substance and a carrier transporting substance.

20. The photoreceptor of claim 19, wherein said carrier transporting substance is selected from the group consisting of trinitrofluorenone, tetranitrofluorenone, poly-N-vinylcarbazole, a triazol derivative, oxadiazol derivative, imidazol derivative, a pyrazolone derivative, polyaryl alkane derivative, phenylene diamine derivative, hydrazone derivative, amine substituted alkene derivative, triaryl amine derivative, carbazole derivative, and stylbene derivative.

21. The photoreceptor of claim 1, wherein the photosensitive layer is a single layer which consists essentially of a binder and said azo compound dispersed therein.

22. The photoreceptor of claim 15, 19, or 21, wherein said photoreceptor has an intermediate layer.

23. The photoreceptor of claim 15, wherein said photoreceptor has an overcoat layer.

24. The photoreceptor of claim 2 or 3, wherein said A is an ethyl group, propyl group, pentyl group, methoxyethyl group, hydroxyethyl group, benzyl group, phenethyl group, or chlorophenyl group.

25. The photoreceptor of claim 2 or 3, wherein said Z is the group of atoms necessary for constituting a substituted or unsubstituted benzene ring, substituted or unsubstituted naphthalene ring, substituted or unsubstituted indole ring, or substituted or unsubstituted carbazole ring.

26. The photoreceptor of claim 2 or 3, wherein A is a substituted or unsubstituted phenyl group.

* * * * *